(12) United States Patent  (10) Patent No.: US 8,712,538 B2
Greenberg et al.  (45) Date of Patent: Apr. 29, 2014

(54) METHOD AND APPARATUS FOR VISUAL NEURAL STIMULATION

(75) Inventors: Robert J. Greenberg, Los Angeles, CA (US); Matthew J. McMahon, Los Angeles, CA (US); Chris Sekirnjak, Denver, CO (US); E. J. Chichilnisky, Del Mar, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 12/789,275

(22) Filed: May 27, 2010

(65) Prior Publication Data

US 2010/0236062 A1  Sep. 23, 2010

Related U.S. Application Data

(62) Division of application No. 11/592,804, filed on Nov. 3, 2006.

(60) Provisional application No. 60/733,701, filed on Nov. 3, 2005.

(51) Int. Cl.
*A61N 1/00* (2006.01)

(52) U.S. Cl.
USPC .............................. 607/54; 607/116; 607/152

(58) Field of Classification Search
USPC .............. 607/116, 118, 137, 141, 152, 59, 54
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,877,866 B1 * | 2/2011 | Greenberg et al. | 29/829 |
| 2002/0193845 A1 * | 12/2002 | Greenberg et al. | 607/54 |
| 2002/0198573 A1 * | 12/2002 | Nisch et al. | 607/54 |
| 2003/0093066 A1 * | 5/2003 | Peyman | 606/5 |
| 2003/0097166 A1 * | 5/2003 | Krulevitch et al. | 607/116 |
| 2003/0158588 A1 * | 8/2003 | Rizzo et al. | 607/54 |

(Continued)

FOREIGN PATENT DOCUMENTS

WO   WO 2005114720 A2 * 12/2005 .............. H01L 21/50

OTHER PUBLICATIONS

Eugene De Juan, Retinal Tacks, American Journal of Ophthalmology 99: pp. 272-274, Mar. 1985.

*Primary Examiner* — Niketa Patel
*Assistant Examiner* — William Levicky
(74) *Attorney, Agent, or Firm* — Scott B. Dunbar

(57) ABSTRACT

The present invention is a flexible circuit electrode array for stimulating neurons where the electrode are less than 20 μm in size and less than 60 μm apart. The array is preferably arranged in a hexagonal pattern to maximize electrode density, and longer in the horizontal direction to correspond to a normal visual scene. The array includes a polymer base layer, metal traces deposited on the polymer base layer, including electrodes suitable to stimulate neural tissue, and a polymer top layer deposited on the polymer base layer and the metal traces defining openings for the electrodes smaller than the electrodes to overlap the electrodes.

9 Claims, 19 Drawing Sheets

(56) References Cited

U.S. PATENT DOCUMENTS

2003/0233134 A1* 12/2003 Greenberg et al. ............. 607/36
2005/0222624 A1* 10/2005 Greenberg et al. ............... 607/2
2006/0241753 A1* 10/2006 Suaning et al. .............. 623/6.63
2006/0247754 A1* 11/2006 Greenberg et al. ........... 607/137

* cited by examiner 0.25 mm

NETTING
RETINA
GLASS SUBSTRATE
PLATINUM ELECTRODES
SIICONE NITRIDE INSULATION d

A

FIG. 2C
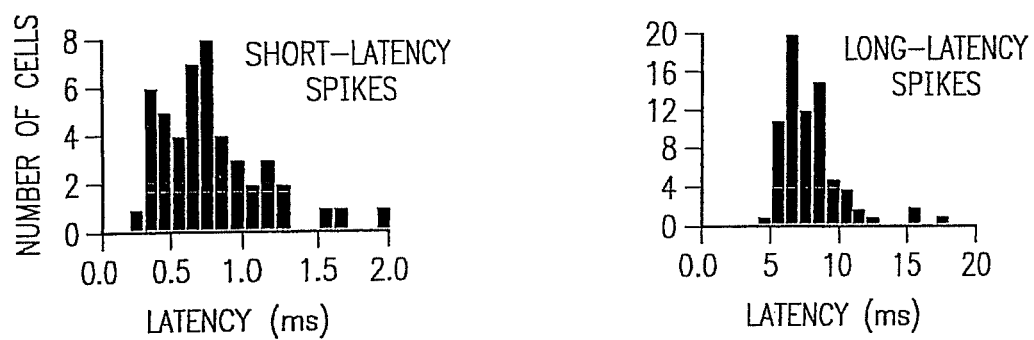
FIG. 3A
FIG. 3B
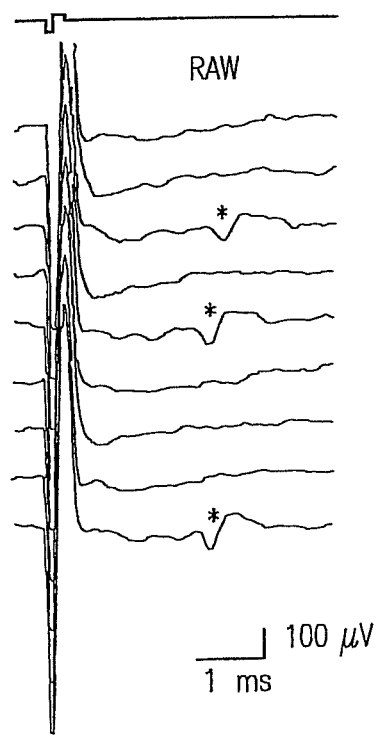
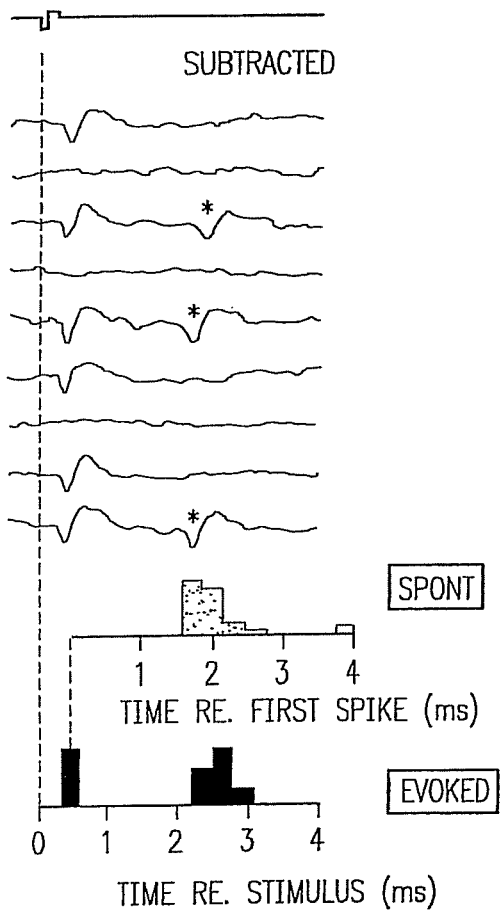

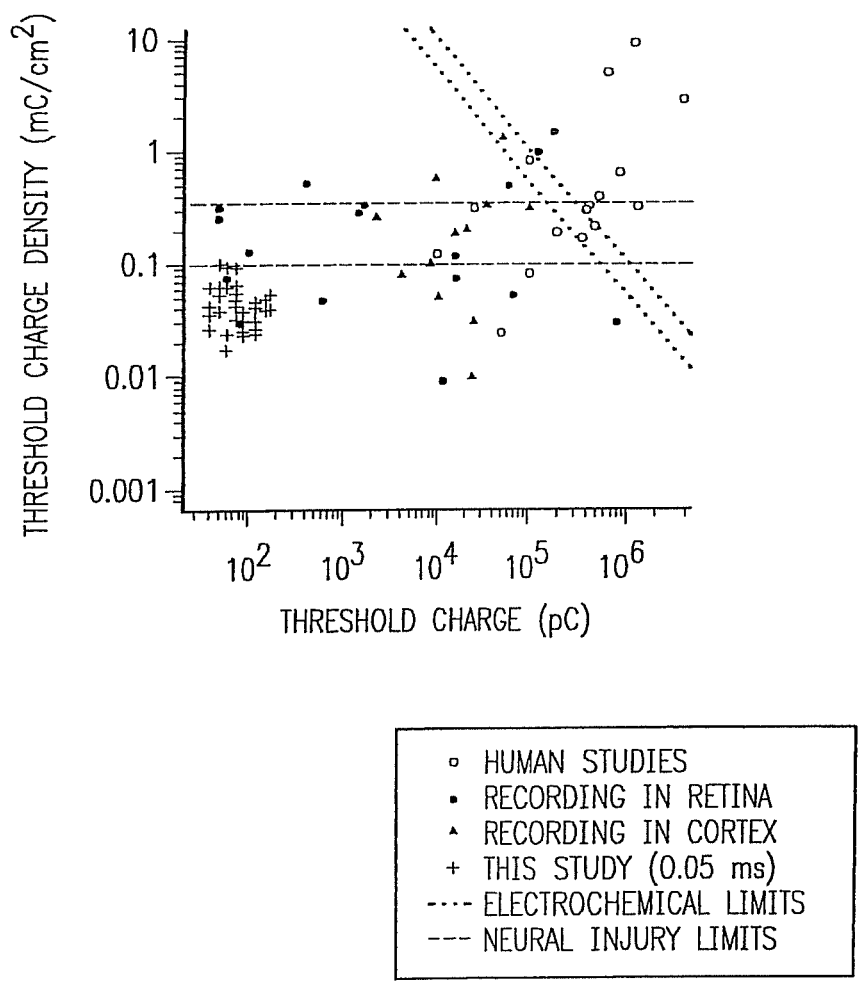

METHOD AND APPARATUS FOR VISUAL NEURAL STIMULATION

CROSS REFERENCE TO RELATED APPLICATIONS

This application is a divisional application of, and claims priority to, U.S. application Ser. No. 11/592,804, filed Nov. 3, 2006, for Method and Apparatus for Visual Neural Stimulation which is related to and claims benefit of U.S. provisional application 60/733,701, for Electrical Stimulation of Mammalian Retinal Ganglion Cells with Multi-Electrode Arrays filed Nov. 3, 2005. This application is related to and incorporates by reference, U.S. patent application Ser. No. 11/207,644 Flexible Circuit Electrode Array filed Aug. 19, 2005.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of providing artificial vision through electrical stimulation of visual neurons.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat.

No. 5,935,155 to Humayun describes a retinal prosthesis for use with the flat retinal array described in de Juan.

Recent attempts to restore vision in the blind have met with extraordinary success. Electrical stimulation of retinas in people with neurodegenerative diseases has demonstrated the potential for direct excitation of neurons as a means of re-establishing sight. Long-term retinal implants in several profoundly blind people were shown to produce perceptions of light and allowed for the detection of motion and discrimination of very simple shapes (Humayun 2003; Humayun et al. 2003). Such achievement brings hope to the millions of people worldwide who suffer from photoreceptor loss due to advanced retinitis pigmentosa or age-related macular degeneration (Heckenlively et al. 1988; Klein et al. 1997). It is expected that ten years from now, macular degeneration will become the single leading cause of legal blindness with an incidence as high as 5.5% in people over 65 (Klein et al. 1997). While degenerative diseases result in severe damage to photoreceptors, inner retinal neurons survive at fairly high rates (Stone et al. 1992; Santos et al. 1997; Kim et al. 2002) and may be electrically excitable. The fundamental concept underlying retinal neuroprosthetic devices is to electrically activate those residual neurons by bypassing the damaged photoreceptors, thus achieving artificial vision in otherwise blind patients. Of several prosthetics designs, epiretinal implants specifically target ganglion cells by positioning electrodes in close proximity to the inner surface of the retina.

In spite of recent successes, the current implants are but a first step toward restoring sight. To create useful vision, stimulating electrodes must be arranged in two-dimensional arrays that generate a visual image made up of a matrix of discrete perceptions of light. Psychophysical studies suggest that foveal implants may provide the user with an acceptable level of mobility if they contain a minimum of about 600 electrodes (Cha et al. 1992a; Cha et al. 1992b). To achieve this number or greater, electrodes must be tightly packed, necessitating small stimulation sites. At present a typical epiretinal implant contains tens of electrodes with diameters of a few hundred μm, spaced several hundred μm apart (Humayun 2003). Considering that such electrodes are much larger than the cells they stimulate, the need for implants with hundreds or thousands of much smaller electrodes is apparent. The success of the next generation of implantable devices will be tied to our understanding of how to activate neurons with extracellular electric stimuli applied to the retinal surface through electrodes that approach cellular dimensions. Little is known about the parameters which would permit reliable retinal stimulation with small electrodes. When the electrode surface area is reduced, current density and charge density increase rapidly, and high charge densities are known to cause tissue damage by electrochemical reactions (Pollen 1977; Brummer et al. 1983; Tehovnik 1996). A detailed in vitro analysis of small electrode stimulation is thus a prerequisite for developing such implants for use in human patients.

A comprehensive literature review reveals that the feasibility of stimulation with arrays of small electrodes in mammalian tissue has not been adequately tested. The majority of studies involving retinal stimulation have used needle-shaped probes with one or two conductors at the end of an insulated rod, such as platinum wires or concentric microelectrodes. In its simplest form, such stimulating probes are made of metal wires several hundred μm in diameter, exposed at the tip and insulated elsewhere (Doty and Grimm 1962; Humayun et al. 1994; Nadig 1999; Weiland et al. 1999; Suzuki et al. 2004).

Others have attempted to utilize stimulating microprobes with tip diameters of 25 μm or smaller (Dawson and Radtke 1977; Wyatt et al. 1994; Rizzo et al. 1997; Jensen et al. 2003).

However, the geometry of such probes differs greatly from the planar disk electrode design developed for current epiretinal implants. Stimulation, furthermore, is always limited to a single stimulation site, precluding the study of stimulation using multiple electrodes and their interaction effects. The use of multi-electrode arrays for retinal stimulation has been mainly limited to large electrodes with diameters between 100 and 1500 μm (Greenberg 1998; Humayun et al. 1999; Hesse et al. 2000; Walter and Heimann 2000; Humayun et al. 2003; Rizzo et al. 2003b). Multi-electrode arrays with smaller electrodes (around 10 μm diameter) have been utilized to stimulate the retina in the subretinal space (Zrenner et al. 1999; Stett et al. 2000). Grumet has used an array to selectively stimulate the axons of retinal ganglion cells, using a separate distant array to record somatic spikes (Grumet 1999; Grumet et al. 2000). No study has targeted mammalian ganglion cell bodies for direct epiretinal stimulation using planar electrodes with surface areas below 200 μm2. In this study we establish thresholds for stimulation of ganglion cells in rat, guinea pig, and primate retina using electrodes with surface areas of 30-500 μm2 (diameters of 6-25 μm). We then used these parameters to further investigate frequency dependence, pharmacology, and spatial interaction effects of stimulation. Our arrays use planar disk microelectrodes very similar to those utilized in present epiretinal prosthetics, but smaller by an order or two of magnitude. We conclude our analysis by discussing the results in the context of the pertinent literature. Early and preliminary portions of this work have been presented elsewhere (Sekirnjak et al. 2005).

SUMMARY OF THE INVENTION

Existing epiretinal implants for the blind are designed to electrically stimulate large groups of surviving retinal neurons using a small number of electrodes with diameters of several hundred μm. To increase the spatial resolution of artificial sight, electrodes much smaller than those currently in use are desirable. In this study we stimulated and recorded ganglion cells in isolated pieces of rat, guinea pig, and monkey retina. We utilized micro-fabricated hexagonal arrays of 61 platinum disk electrodes with diameters between 6 and 25 μm, spaced 60 μm apart. Charge-balanced current pulses evoked one or two spikes at latencies as short as 0.2 ms, and typically only one or a few recorded ganglion cells were stimulated. Application of several synaptic blockers did not abolish the evoked responses, implying direct activation of ganglion cells. Threshold charge densities were typically below 0.1 mC/cm2 for a pulse duration of 100 μs, corresponding to charge thresholds of less than 100 pC. Stimulation remained effective after several hours and at high frequencies. To demonstrate that closely spaced electrodes can elicit independent ganglion cell responses, we utilized the multi-electrode array to stimulate several nearby ganglion cells simultaneously. From these data we conclude that electrical stimulation of mammalian retina with small-diameter electrode arrays is achievable and can provide high temporal and spatial precision at low charge densities. We review previous epiretinal stimulation studies and discuss our results in the context of 32 other publications, comparing threshold parameters and safety limits.

BRIEF DESCRIPTION OF THE DRAWINGS

FIG. 1 B is side view of the preferred retinal array.

FIG. 1 C is a waveform showing a stimulation pattern.

FIG. 13 is a graph showing threshold charge density vs. charge.

DETAILED DESCRIPTION OF THE PREFERRED EMBODIMENTS

Figure 1A:
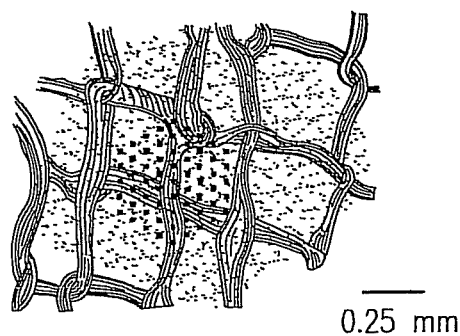
FIG. 1 A is planar view of the distribution of electrodes in the referred retinal array over retinal tissue.

The following description is of the best mode presently contemplated for carrying out the invention. This description is not to be taken in a limiting sense, but is made merely for the purpose of describing the general principles of the invention. The scope of the invention should be determined with reference to the claims.

Recent attempts to restore vision in the blind have met with extraordinary success. Electrical stimulation of retinas in people with neurodegenerative diseases has demonstrated the potential for direct excitation of neurons as a means of re-establishing sight. Long-term retinal implants in several profoundly blind people were shown to produce perceptions of light and allowed for the detection of motion and discrimination of very simple shapes (Humayun 2003; Humayun et al. 2003). Such achievement brings hope to the millions of people worldwide who suffer from photoreceptor loss due to advanced retinitis pigmentosa or age-related macular degeneration (Heckenlively et al. 1988; Klein et al. 1997). It is expected that ten years from now, macular degeneration will become the single leading cause of legal blindness with an incidence as high as 5.5% in people over 65 (Klein et al. 1997). While degenerative diseases result in severe damage to photoreceptors, inner retinal neurons survive at fairly high rates (Stone et al. 1992; Santos et al. 1997; Kim et al. 2002) and may be electrically excitable. The fundamental concept underlying retinal neuroprosthetic devices is to electrically activate those residual neurons by bypassing the damaged photoreceptors, thus achieving artificial vision in otherwise blind patients. Of several prosthetics designs, epiretinal implants specifically target ganglion cells by positioning electrodes in close proximity to the inner surface of the retina. In spite of recent successes, the current implants are but a first step toward restoring sight. To create useful vision, stimulating electrodes must be arranged in two-dimensional arrays that generate a visual image made up of a matrix of discrete perceptions of light. Psychophysical studies suggest that foveal implants may provide the user with an acceptable level of mobility if they contain a minimum of about 600 electrodes (Cha et al. 1992a; Cha et al. 1992b). To achieve this number or greater, electrodes must be tightly packed, necessitating small stimulation sites. At present a typical epiretinal implant contains tens of electrodes with diameters of a few hundred μm, spaced several hundred μm apart (Humayun 2003). Considering that such electrodes are much larger than the cells they stimulate, the need for implants with hundreds or thousands of much smaller electrodes is apparent. To match the intrinsic resolution of the visual system, an advanced implant would devote one electrode to every ganglion cell. This requires that each electrode be similar in size to a ganglion cell (about 5-20 μm). Instead of 4 affecting hundreds or thousands of cells, each electrode would evoke a few spikes in a few retinal ganglion cells.

The success of the next generation of implantable devices will be tied to our understanding of how to activate neurons with extracellular electric stimuli applied to the retinal surface through electrodes that approach cellular dimensions. Little is known about the parameters which would permit reliable retinal stimulation with small electrodes. When the electrode surface area is reduced, current density and charge density increase rapidly, and high charge densities are known to cause tissue damage by electrochemical reactions (Pollen 1977; Brummer et al. 1983; Tehovnik 1996). A detailed in vitro analysis of small electrode stimulation is thus a prerequisite for developing such implants for use in human patients.

A comprehensive literature review reveals that the feasibility of stimulation with arrays of small electrodes in mammalian tissue has not been adequately tested. The majority of studies involving retinal stimulation have used needle-shaped probes with one or two conductors at the end of an insulated rod, such as platinum wires or concentric microelectrodes. In its simplest form, such stimulating probes are made of metal wires several hundred μm in diameter, exposed at the tip and insulated elsewhere (Doty and Grimm 1962; Humayun et al. 1994; Nadig 1999; Weiland et al. 1999; Suzuki et al. 2004). Others have attempted to utilize stimulating microprobes with tip diameters of 25 μm or smaller (Dawson and Radtke 1977; Wyatt et al. 1994; Rizzo et al. 1997; Jensen et al. 2003). However, the geometry of such probes differs greatly from the planar disk electrode design developed for current epiretinal implants. Stimulation, furthermore, is always limited to a single stimulation site, precluding the study of stimulation using multiple electrodes and their interaction effects.

The use of multi-electrode arrays for retinal stimulation has been mainly limited to large electrodes with diameters between 100 and 1500 μm (Greenberg 1998; Humayun et al. 1999; Hesse et al. 2000; Walter and Heimann 2000; Humayun et al. 2003; Rizzo et al. 2003b). Multi-electrode arrays with smaller electrodes (around 10 μm diameter) have been utilized to stimulate the retina in the subretinal space (Zrenner et al. 1999; Stett et al. 2000). Grumet has used an array to selectively stimulate the axons of retinal ganglion cells, using a separate distant array to record somatic spikes (Grumet 1999; Grumet et al. 2000). No study has targeted mammalian ganglion cell bodies for direct epiretinal stimulation using planar electrodes with surface areas below 200 μm2.5 In this study we establish thresholds for stimulation of ganglion cells in rat, guinea pig, and primate retina using electrodes with surface areas of 30-500 μm2 (diameters of 6-25 μm). We then used these parameters to further investigate frequency dependence, pharmacology, and spatial interaction effects of stimulation. Our arrays use planar disk microelectrodes very similar to those utilized in present epiretinal prosthetics, but smaller by an order or two of magnitude. We conclude our analysis by discussing the results in the context of the pertinent literature. Early and preliminary portions of this work have been presented elsewhere (Sekirnjak et al. 2005).

Methods

Retinal Preparation

This study used retinal tissue from 55 adult rats, 6 guinea pigs, and one macaque monkey. The average body weight was 289±5 g for rats (Long-Evans), 420±55 g for guinea pigs, and 4 kg for the macaque monkey (*Macaca radiata*). Rodent eyes were enucleated after decapitation of animals deeply anesthetized with 10 mg/kg Xylazine and 50 mg/kg Ketamine HCl. Primate eyes were obtained from terminally anesthetized macaque monkeys used by other experimenters, in accordance with institutional guidelines for the care and use of animals. Immediately after enucleation, the anterior portion of the eye and vitreous were removed in room light and the eye cup placed in bicarbonate-buffered Ames' solution. Vitreous removal in rats was aided by a homemade extractor which allowed for rapid but gentle separation of retina and vitreous gel. The success rate for vitrectomies performed in this manner was 92%. Pieces of retina 1-2 mm in diameter (FIG. 1A) were separated from the retinal pigment epithelium and placed flat on the electrode array, with the ganglion cell layer facing the array (FIG. 1B). The tissue was held in place by weighted nylon netting positioned over the array. The preparation was then mounted on a circuit board attached to an inverted microscope and continuously superfused at room temperature with Ames' solution bubbled with 95% oxygen and 5% carbon dioxide at a flow rate of 2-4 ml/min. Pharmacological agents (TTX, kynurenic acid, CNQX, AP-5, cadmium chloride) were added directly to the perfusion solution.

Multi-electrode Array

Figure 1B:
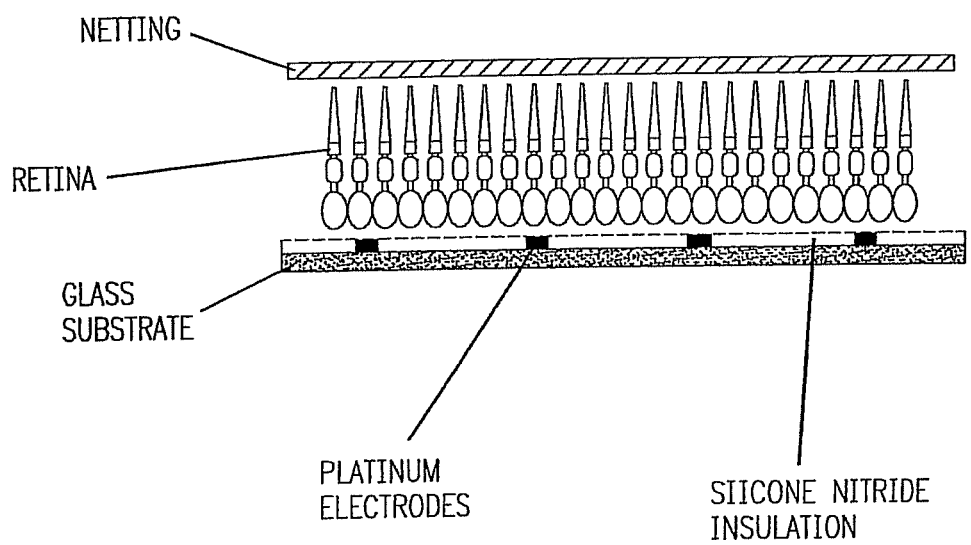

The array consisted of a planar hexagonal arrangement of 61 extracellular electrodes, approximately 0.5×0.5 mm2 in total size (FIG. 1A). These electrodes were used both to record action potentials extracellularly from ganglion cells (Meister et al. 1994; Chichilnisky and Baylor 1999), and to apply current to the tissue for stimulation. In some experiments, different neighboring electrodes were used for stimulating and recording.

The array was microfabricated on a glass substrate, with indium tin oxide leads and silicon nitride insulation (Litke 1998; Litke et al. 2003). Each electrode was formed by microwells (holes in the silicon nitride layer) which were electroplated with platinum prior to an experiment (FIG. 1A, B). This was accomplished by submersing the array in a 0.0025N HCl solution containing 1% chloroplatinic acid and 0.01% lead acetate and applying voltages of 1-5 V through 10 MΩ resistors for 10-120 sec. Electrode size was determined by well diameter (5, 6, 8, 10, 12, or 14 µm) as well as the amount of platinum deposited in each well. Final electrode diameter varied between approximately 6 and 25 µm, with a fixed inter-electrode spacing of 60 µm. The geometric electrode area (#r2) was used to calculate current and charge densities; however, platinum tends to deposit in a granular fashion, rendering the effective electrode area significantly larger (Mathieson et al. 2004). A circular chamber glued on the glass plate allowed for perfusion of saline solution. A 4 cm-long platinum wire loop integrated into the chamber served as distant ground. All stimulations were performed using a monopolar configuration (electrode to distant ground).

Electrical Stimulation and Recording

Unless otherwise noted, experiments were performed on a setup allowing for simultaneous recording of all 61 electrodes and stimulation on multiple electrodes. The array was connected to a circuit board containing two custom-made readout ASICs (Application Specific Integrated Circuit) which amplified, filtered, and multiplexed signals from the 61 electrodes and sent them to ADC cards installed in a PC. The board also contained two computer controlled ASICs capable of sending current pulses to any configuration of electrodes (Dabrowski et al. 2005). A dim level of illumination was maintained during the entire experiment (room lights or microscope illuminator). Recording and stimulation were controlled by interface software (Labview). Extracellular potentials were recorded from all 61 electrodes, digitized at 20 kHz (Litke 1999), and stored for off-line analysis.

Figure 1C:
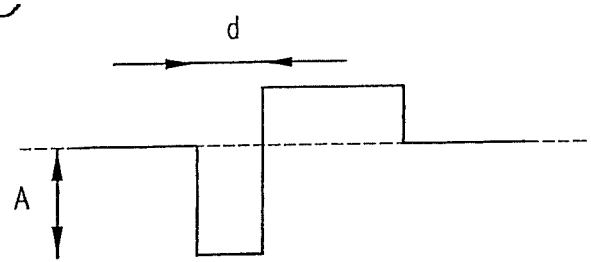
Figure 6:
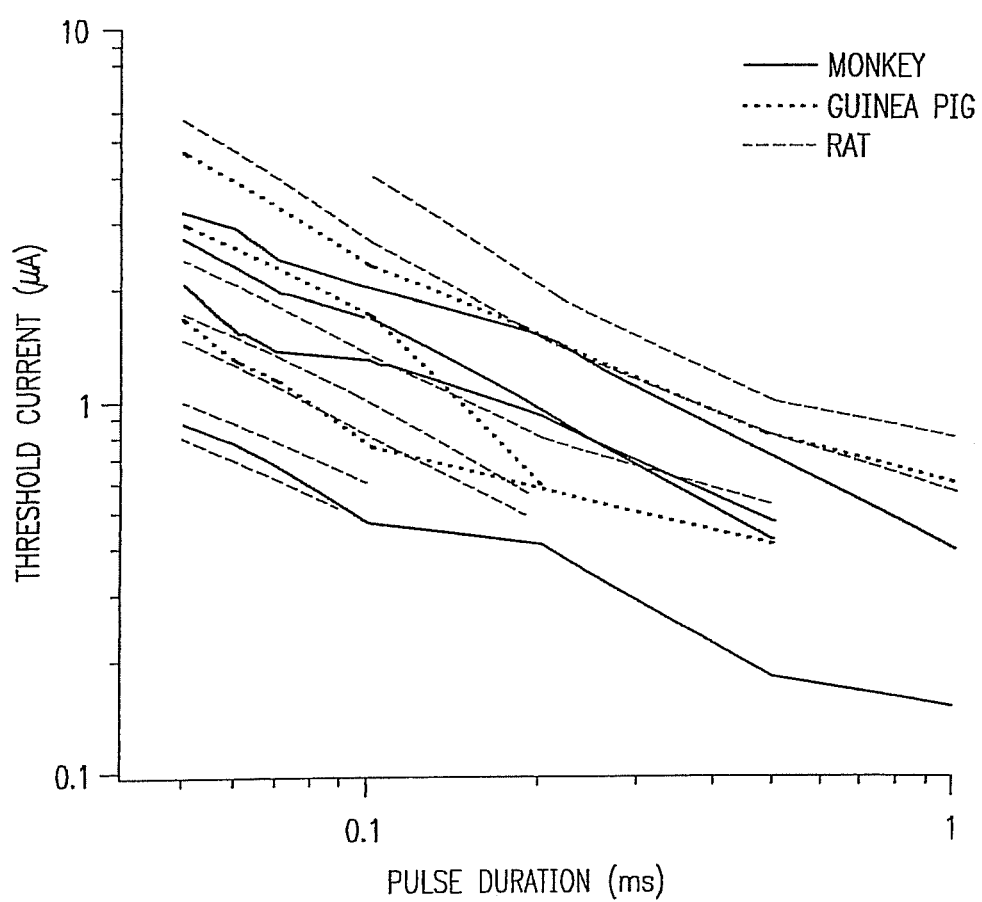
FIG. 6 is a strength duration curve.

The available discrete stimulation pulse current amplitudes were: 0.6, 0.8, 1.0, 1.2, 1.5, 1.7, 2.0, 2.3, 2.7, 3.0, 3.3, 4.0, 4.7, 5.3, 6.0, 6.7, 8.0, 9.3, 10.7, 12.0, 13.3, and 16.7 µA (several threshold curves reported in FIG. 6 were determined using an earlier stimulus generator capable of delivering current amplitudes as low as 0.1 µA. This device was not used in subsequent experiments). The pulse consisted of a cathodic (negative) current pulse of amplitude A and duration d, followed immediately 8 by an anodic (positive) pulse of amplitude A/2 and duration 2d (FIG. 1C). Reported current values always refer to the negative phase amplitude A. Pulse duration was 0.05, 0.1, 0.2, 0.5, or 1 ms and always refers to the duration d of the cathodic phase. All pulses were individually calibrated to produce biphasic stimuli with zero net charge. The pulse shape could be inverted in time to yield an anodic-first stimulus. Stimulation frequency was varied between 0.25 and 300 Hz. Experimental protocol Many ganglion cells show maintained activity under diffuse retinal illumination (Troy and Robson 1992) and fire spontaneous spikes in isolated pieces of retina. Stimulation on a particular electrode was typically attempted if spontaneous extracellular spikes could be recorded from that electrode. This approach guaranteed that the electrode was properly platinized and confirmed that ganglion cells in the vicinity of the electrode were alive. Typically, at least half of the platinized electrodes on an array showed spontaneous activity from at least one cell. Spontaneous spikes were readily distinguished from evoked spikes since they bore no temporal relationship to the stimulus pulse, while evoked spikes were locked to the stimulus onset. Stimulation was typically attempted by using the lowest current settings and was then increased systematically if no response was seen. Threshold was defined as the current setting which produced a spike with nearly every stimulus pulse (≥90% of trials) while stimulating at 1-2 Hz. Latency was defined as the time between stimulus pulse onset and the first deflection of the evoked spike. Unless otherwise stated, threshold current, threshold charge, and threshold charge density always refer to the negative phase of the biphasic, charge-balanced stimulus pulse. For pharmacological manipulations, a minimum drug perfusion time of 5-10 minutes was allowed before responses were recorded.

Data Analysis

Multi-electrode data was analyzed offline using Labview, Matlab, and Igor Pro. Means and group data were calculated in Microsoft Excel. Images were processed in Adobe Photoshop. 9 Chronaxies were calculated by fitting power functions $y=a/x+b$ and $y=a/x^p+b$ (Lapicque 1907; Ranck 1975; Holsheimer et al. 2000) or exponentials $y=b/(1-e^{-x/a})$ (Lapicque 1907; Plonsey and Barr 1988; Greenberg 1998) to the strength-duration data. The asymptote (coefficient b) was defined as the rheobase; chronaxie was calculated as $(a/b)1/p$, $a/b$, or $a \ln 2$ for power and exponential fit functions, respectively. Given the small number of data points available for some cells, fit quality and resulting parameters differed for the individual functions and thus values from all three are reported in the Results section. Autocorrelations of evoked and spontaneous spiking were obtained by generating histograms of spike times and interspike intervals, respectively. On average, about 37 spikes were used per histogram. Spontaneous histograms were aligned so that time=0 coincided with the occurrence of the peak of the first evoked spike.

Power function fit lines to literature data and R2 values were calculated in Igor Pro by fitting linear functions to the logarithmic plots of threshold parameters. Statistical comparisons were done by performing a Student t-test (two-tailed, equal variance) with a significance limit of p<0.05. Errors and error bars reported in this study are standard errors of the mean (SEM), unless otherwise stated.

Figure 4A:
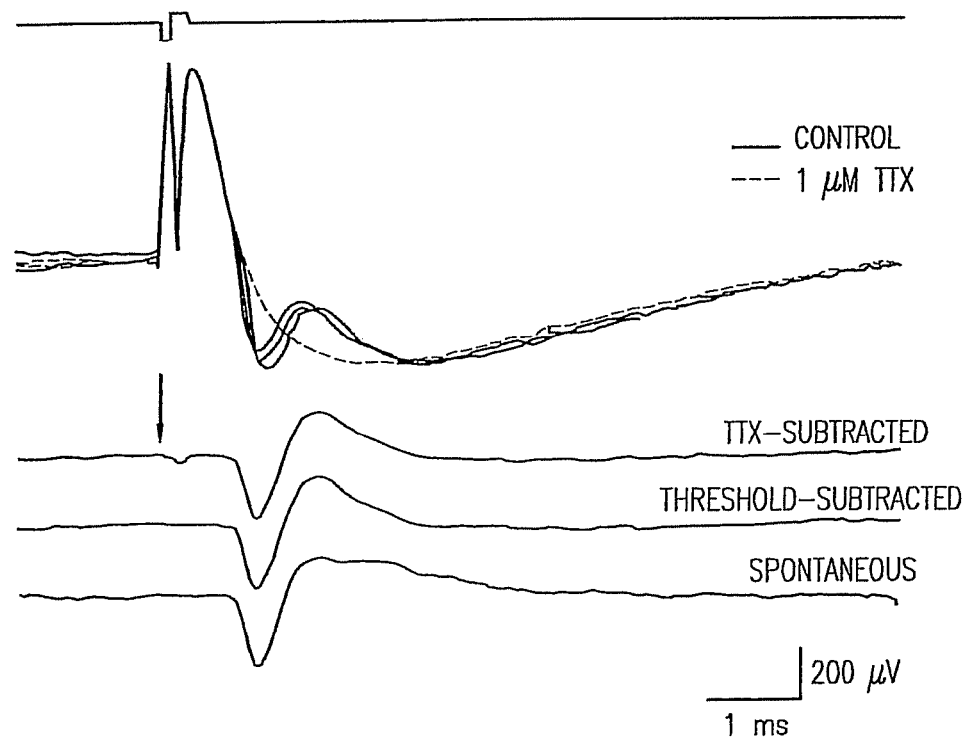
FIG. 4 A-C are waveforms showing the results of pharmacological manipulations.

Threshold artifact subtraction To reveal spikes with latencies of less than 2 ms, a novel digital subtraction technique was used. Spikes obscured by the stimulation artifact (which typically lasted for several milliseconds) were made visible by increasing the stimulation current until a possible spike threshold was reached. Just below threshold, the recorded traces changed shape noticeably on about half of the stimulus trials (for example, a change in curvature or peak height), indicating that a possible spike hidden inside the artifact was elicited on some trials (see FIG. 2B). Subsequently, the digital difference between two such traces was calculated. Since the artifact itself was identical in both traces, the subtraction cleanly revealed the spike inside the stimulus artifact. Typically, several traces with and without a suspected spike were averaged before subtraction to increase the signal over the noise. This method necessitated recording the spikes on an electrode immediately adjacent to the stimulation electrode, since the signal recorded at the stimulation site usually saturated the amplifier and was not suitable for subtraction. The results obtained were comparable to or better than those reported for artifact suppression by local curve fitting (Wagenaar and Potter 2002). We further verified this technique in 6 cells by applying tetrodotoxin (TTX, 1 µM) to the bath solution. The stimulus artifact recorded in TTX was then subtracted from the traces containing obscured spikes. In these cells, the resulting subtracted spikes were identical to the spikes obtained using the above method. An example of this is shown in FIG. 4A.

Literature Analysis

Data from epiretinal stimulation studies were compiled as follows. Threshold current, current density, charge, and charge density necessary to elicit a ganglion cell response were median or mean values as reported in each study. When a list of thresholds was reported, an average value was calculated; when a range of thresholds was reported, the minimum or the median value was used; in some cases, a "typical" value was taken from a representative example or figure. Whenever possible, a missing parameter was calculated from reported parameters, for instance threshold current from reported threshold charge (Humayun et al. 1999; Suzuki et al. 2004), surface area from charge density (Dawson and Radtke 1977), or current from reported charge density (Nadig 1999). In a few cases it was not possible to calculate a parameter and it was then estimated from other publications by the same author or the same group (asterisks in Table 1). When such substitution was not possible, the study was not included (Crapper and Noell 1963; Benjamin et al. 1994; Narayanan et al. 1994; Kuras and Gutmaniene 1997). Several studies were represented by multiple entries when different values of parameters were reported (electrode size, duration, pulse shape) or when several drastically different results were reported for the same parameters (such as for two or more human subjects). The geometric surface area was calculated from the reported electrode geometry (circular or rectangular for planar electrodes: $\pi r^2$ or $l2$, cylindrical for exposed wires: $\pi r 2h$, conical for cone tips: $\pi r(r2+h2)1/2$, spherical for ball electrodes: $4\pi r^2$). When two or more electrodes were reported to be coupled electrically and used simultaneously, the surface area was multiplied accordingly. When a stimulus consisted of high frequency pulse trains, the effective pulse duration was taken as the number of pulses per train times the single-pulse duration (Walter and Heimann 2000; Laube et al. 2003). Whenever possible, data from normal animals, not those with degenerated retinas were used.

For plotting the neural injury limit, cat cortical tissue data from McCreery et al. (1990) was fit to the equation $\log(Q/A) = k - \log(Q)$, where Q is the charge in nC and Q/A is the charge density in mC/cm2 (Shannon 1992; Merrill et al. 2005). The data can be fit with a coefficient k varying between 1.7 and 2.0; both values were used for the injury limit plots in FIG. 13.

Results

We electrically stimulated pieces of isolated mammalian retina while simultaneously recording spiking activity in ganglion cells. The properties of evoked spikes are presented first, followed by strength-duration relationships, temporal properties, and the results from multi-electrode stimulation. Stimulation at individual array electrodes resulted in all-or-none spikes recorded at latencies between a few hundred µs and tens of ms. Of the 208 successfully stimulated ganglion cells, 189 were from rat, 11 from guinea pig, and 8 from monkey. Most responses consisted of one or two spikes, although in some cells later spikes were recorded.

Response Latencies

Figure 2A:
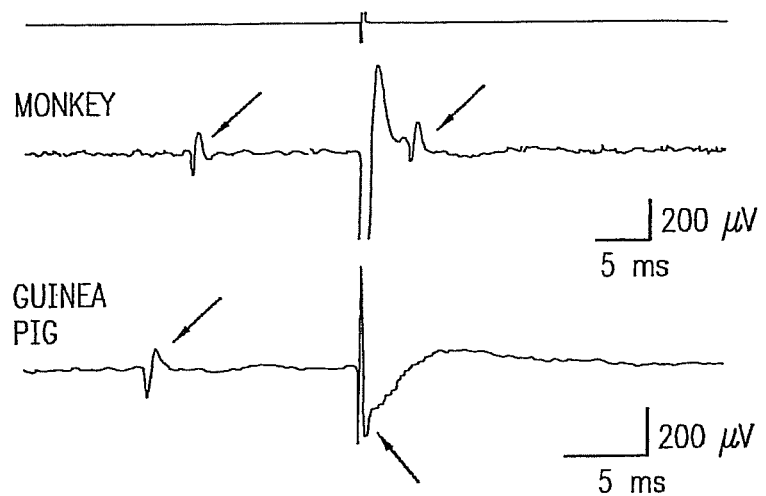
FIG. 2 A-C are waveforms of evoked responses.
Figure 2B:
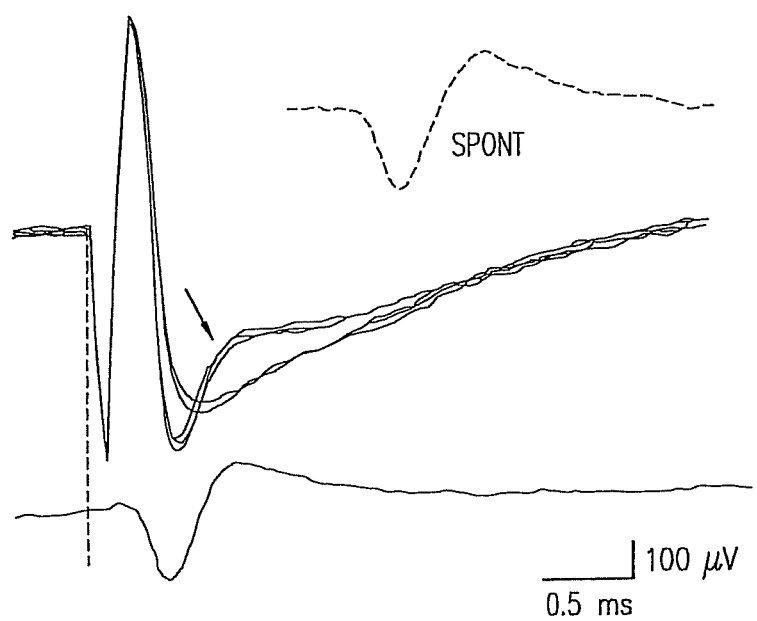

We classified spikes with latency ≥2 ms as long-latency spikes, and earlier responses as shortlatency. Latencies above 10 ms were infrequently observed and virtually no spikes occurred more than 20 ms after stimulation onset. Typically, only long-latency spikes could be readily discerned since the stimulus artifact obscured the first few milliseconds of the recording. FIG. 2A shows two spontaneously firing ganglion cells and their responses to single stimulus pulses. While the primate cell (top) responded with a distinct spike at latency 5.6 ms, the guinea pig response (bottom) was obscured by the stimulus artifact. To isolate the evoked short-latency spike, a threshold artifact subtraction method was employed (see Methods). Briefly, the artifact was selectively eliminated by recording several traces near threshold and subtracting those traces which did not contain evoked spikes (FIG. 2B). This method was typically employed when a neighboring electrode was used for stimulation in lieu of the recording electrode, since this configuration reduced the artifact below amplifier saturation levels and allowed the artifact to be subtracted. The result for the guinea pig cell is shown at the bottom of FIG. 2B: a spike was revealed at 0.25 ms latency. For 86 spikes in rat, visible without artifact subtraction, the average latency was 7.6±0.3 ms, while 48 artifact-subtracted spikes had a latency of 0.73±0.05 ms. Nearly all short-latency spikes occurred at <1 ms; the shortest latencies recorded in this study were around 0.2 ms. Latency histograms for both short- and long latency spikes are shown in FIG. 2C.

Evoked spikes usually resembled the recorded spontaneous spikes, but occasionally spikes from a different cell were elicited. Short-latency spikes in particular tended to be of identical shape as the spontaneous spikes. This is shown in the inset of FIG. 2B: the evoked spike resembled the spontaneous spike. Two further examples are shown in FIG. 4A and in the inset to FIG. 8B. Of 48 subtracted short latency spikes, 42 unambiguously matched the spontaneous spike.

Figure 3C:
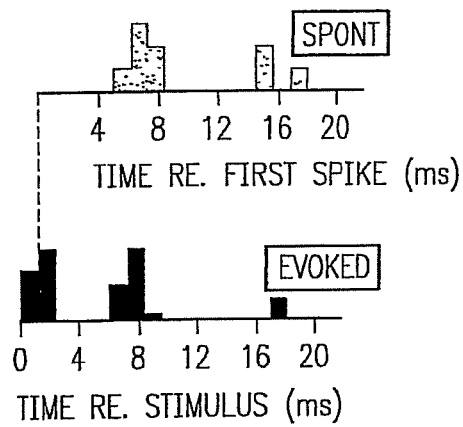
FIG. 3 A-D are waveforms showing the relationship between short and long latency spikes.
Figure 3D:
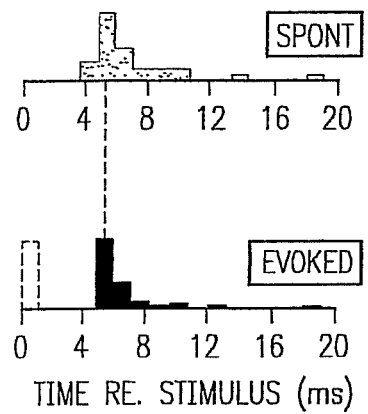

To elucidate the origin of long-latency spikes, the method of digital artifact subtraction was applied to recordings which contained both short- and long-latency spikes. It seemed possible that each long latency spike was in fact the second spike of a pair response and not a solitary spike. Indeed, analysis of 20 cells revealed that the occurrence of long-latency spikes (6.4±0.3 ms) was always associated with short-latency responses (0.7±0.1 ms). An example from guinea pig retina is shown in FIG. 3: while the raw data traces (A) showed only three long-latency spikes (asterisks), the artifact-subtracted traces (B) revealed that every long-latency spike was preceded by a short-latency spike at 0.35 ms. Furthermore, an analysis of spontaneous spiking activity showed that spike doublets spontaneously occurred in this cell. This is shown at the bottom of FIG. 3B: the autocorrelation histogram of spontaneous spikes showed a peak at a latency similar to that of the evoked long-latency spikes. Thus, the evoked spikes occurred with timing expected from the spontaneous activity. A second example from rat retina is shown in FIG. 3C for a cell with long-latency spikes at 7 ms. Spike timing analyses were performed in a total of 8 cells, with similar results: the spontaneous interspike intervals matched the typical intervals between short- and long-latency spikes. These results indicate that some cells responded to a single stimulus pulse with a spike pair, with the first spike obscured by the artifact, and that this tendency toward paired spiking was evident in the spontaneous activity of the cell. The method of analyzing spike timing was further utilized to calculate the approximate latency of obscured short-latency spikes when only long-latency spikes were available. FIG. 3D shows an example of a cell in which a large stimulus artifact precluded the use of the artifact subtraction method; only long-latency spikes were discernible. By aligning the peaks of the two histograms, a short-latency spike (dashed box) was inferred at times ms. Similar results were found in 3 cells and suggest that short-latency responses can be deduced from the observance of long-latency spikes. Lastly, we compared the spike latencies of long-latency responses evoked with stimulation electrodes of different diameters, which ranged from 6 to 25 µm in this study. No systematic difference was observed when large rather than small electrodes were used and average latencies for the smallest electrodes (6-9 µm) were similar to the largest (20-25 µm): 8.2±0.7 ms and 7.1±0.4 ms, respectively ($p>0.2$; $n=32$ cells).

Pharmacological Manipulations

Figure 4B:
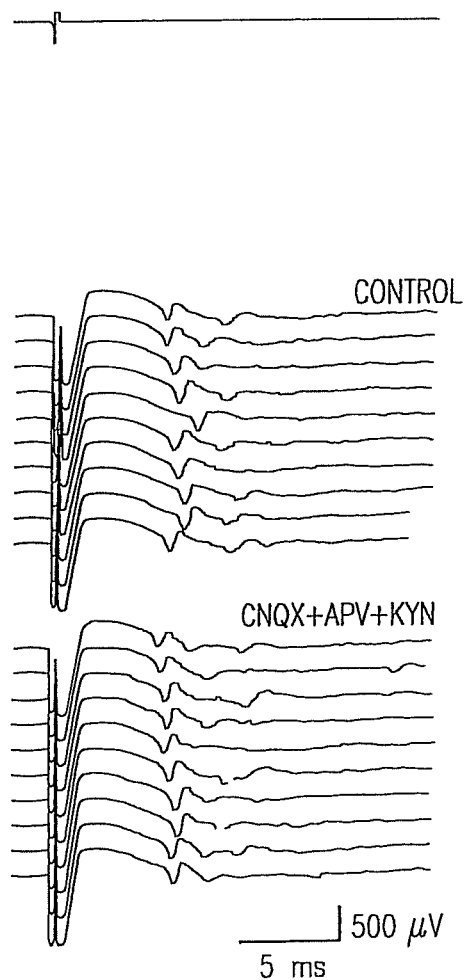
Figure 4C:
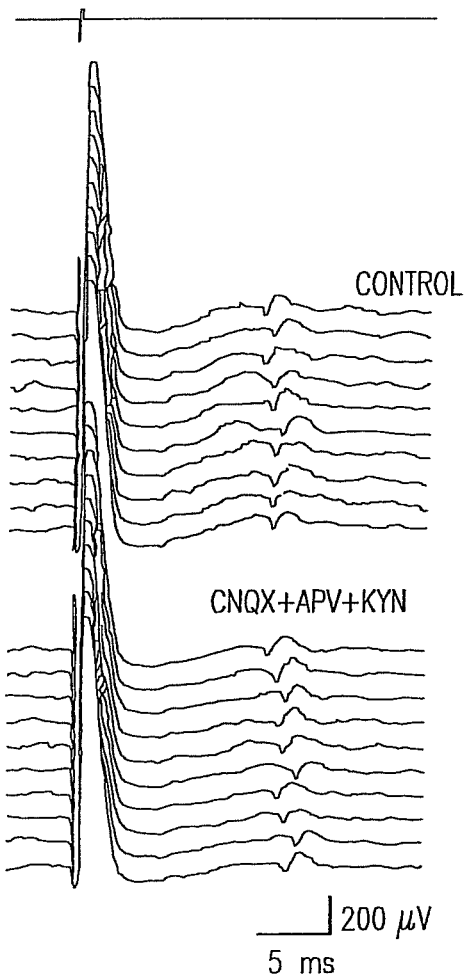

Several ion channel antagonists were applied to the perfusion solution to further investigate the evoked responses. To ascertain that the observed spikes were of neuronal origin, the sodium channel blocker tetrodotoxin (TTX, 1 µM) was added to the perfusion solution. In 3 guinea pig and 17 rat cells, all spikes (both spontaneous and evoked) disappeared within seconds of drug application, confirming their identity as neuronal action potentials. An example is shown in FIG. 4A: application of TTX eliminated evoked short-latency spikes, leaving only the pulse artifact. When this artifact was subtracted from the control responses, an evoked spike was revealed (FIG. 4A). The waveform of this spike did not differ from that derived by threshold artifact subtraction or the spontaneous spike recorded at this electrode (FIG. 4A, bottom). Similar results were found in 5 cells To investigate whether the applied current pulses acted directly on ganglion cells or involved more distant cells with synaptic connections to the recorded cell, blockers of synaptic transmission were added to the perfusion solution. A combination of the following agents was used: the broad spectrum glutamate antagonist kynurenic acid (1 mM), the NMDA-receptor blocker APV (400 µM), and the AMPA-receptor blocker CNQX (75 µM). FIGS. 4B and C show examples of responses from two cells, recorded before and after addition of the blockers. Spike shapes, latencies, and response rates were unchanged, even in the cell with spikes at latency 15 ms (FIG. 4C). No systematic differences between spikes elicited in control and drug conditions were observed in any of 9 cells. These findings suggest that ganglion cells were activated directly, not trans-synaptically, and further corroborate the notion that apparent long-latency spikes (such as in FIG. 4B, C) are not solitary spikes, but part of a two-spike response.

In separate experiments, the calcium channel blocker cadmium chloride (100-250 µM) was applied to the perfusion solution to abolish synaptic transmission (not shown). In 10 cells, evoked spikes were still observed after drug application, indicating that the observed spikes were not produced by mechanisms involving calcium-dependent synaptic transmission. Minimal thresholds and spatial spread Spikes were evoked in ganglion cells using currents between 0.6 and 5 µA. When stimulated with 0.1 ms pulses, the average threshold current for 78 rat cells stimulated under similar conditions was 0.81±0.03 µA, corresponding to a charge of 81±3 pC and a charge density of 0.073±0.005 mC/cm2. In many cases, the lowest current setting of our stimulator (0.6 µA) yielded a superthreshold response, indicating that the reported average thresholds may be overestimated.

Figure 5A:
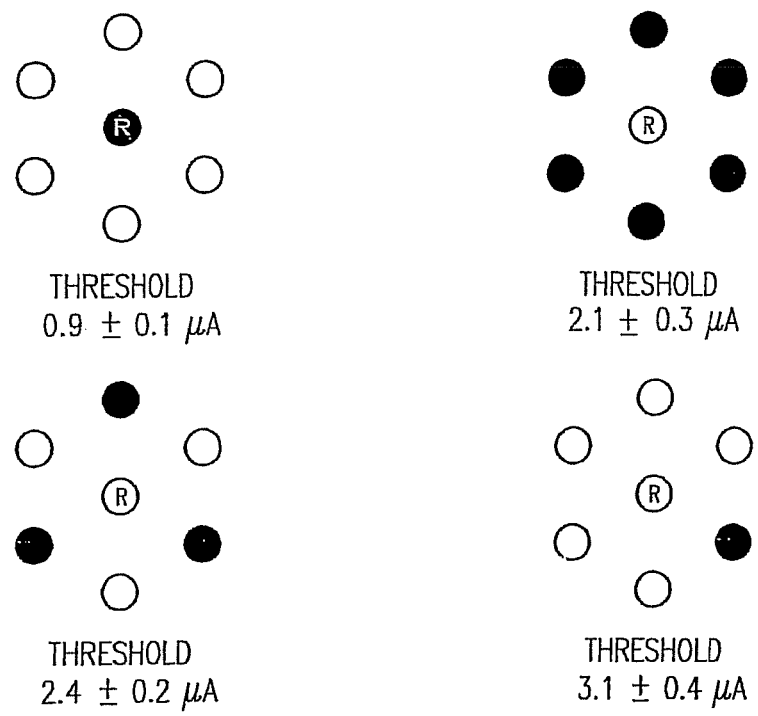
FIG. 5 A-B are diagrams showing the spatial spread of stimulation.

Thresholds were lowest when the recording electrode, rather than a neighboring electrode, was also used for stimulation. To examine whether spikes could be elicited by stimulating at a distance from the recording site, electrodes immediately adjacent to the recording electrode were used to stimulate. FIG. 5A shows average results for 8 cells, stimulated with 1, 3, or 6 adjacent electrodes. The goal was to elicit the same long-latency spike using the different configurations of stimulation sites shown. Thresholds for spike initiation increased several-fold, depending on the number of active electrodes. In particular, when a single neighboring electrode was used for stimulation, about 3 times more current was needed compared to stimulation at the recording electrode. This indicates that a resolution of the order of the electrode spacing or finer (≤60 µm) can be achieved with minimal threshold stimulation.

The preceding results suggest that stimulation using low stimulus amplitudes (<0.1 mC/cm2) usually affected only cells in the vicinity of the stimulation electrode. To further verify this, in 35 low amplitude stimulation experiments (average charge density 0.071±0.004 mC/cm2), all electrodes surrounding the stimulation electrode were inspected for evidence of evoked spikes which differed in latency, shape, or reliability from the ones recorded on the center electrode. Such additional spikes would indicate recruitment of neurons at nearby locations. Of 186 neighboring electrodes analyzed for long-latency spikes, only one showed an additional evoked spike. However, additional evoked spikes were frequently seen on surrounding electrodes when the current was increased several-fold, suggesting recruitment of cells tens of µm distant, consistent with the results shown in FIG. 5A. Still higher currents sometimes elicited spikes on non-neighboring electrodes, more than 150 µm away from the stimulation electrode.

Figure 5B:
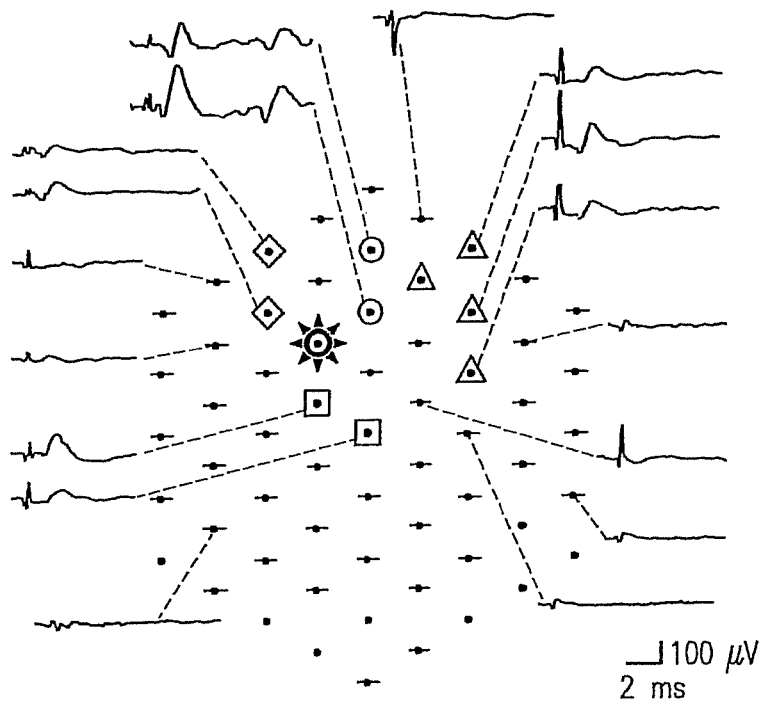

To further investigate spatial spread of activation, a more detailed analysis was performed to detect short-latency spikes around the stimulation electrode. In 4 experiments, we applied TTX and subtracted the averaged stimulus artifact on each electrode individually to reveal additional short latency spikes, as in FIG. 4A. In 2 such experiments with a stimulus strength of around 0.1 mC/cm2, no short-latency spikes were found outside the 60 µm radius around the stimulation electrode. In 2 further experiments stimulated at 0.21 and 0.35 mC/cm2, spikes were detected as far away as 160 μm. One example of strong-stimulus stimulation is illustrated in FIG. 5B: while the majority of electrodes on the array recorded no evoked spikes, four separate responses were elicited in the vicinity of the stimulation site. The spikes from these stimulated cells were each detected on 2 or more electrodes and the electrode recording the largest spike amplitude can be used to infer the approximate location of the soma. Most evoked spikes (circles, squares, diamonds) were recorded within 60 μm of the stimulation electrode, but one cell was detected nearly 160 μm away (triangles). These results show that the radius of stimulated ganglion cells can be controlled by adjusting the stimulus strength.

The above results were obtained by applying cathodic-first pulses (FIG. 1C). For most cells, thresholds were slightly higher when the anodic phase was delivered first: in 18 cells stimulated with 0.05 or 0.1 ms anodic-first pulses, spike thresholds were 115±5% of the thresholds measured using cathodic-first pulses.

Strength-duration Relationship

The current required to elicit a spike depended strongly on pulse duration. In all three species tested, higher currents were required to evoke a spike when shorter pulses were applied. Durations were varied from 50 μs to 1 ms and several resulting strength-duration curves are shown in FIG. 6. In the examples plotted here, electrode diameter, stimulation configuration, and spike latency differed considerably across cells, resulting in a wide spread of threshold curves. Nevertheless, the slopes of these curves were similar in monkey, guinea pig, and rat, indicating that the threshold-duration relationship was independent of the species. To characterize each strength-duration curve by a time-constant and an asymptote, power functions or exponentials were fit to the data (see Methods). Rheobase is defined as the asymptote of the fit curve (Ranck 1975; Loeb et al. 1983) and chronaxie, the classical measure of responsiveness of a neuron, as the duration at which the threshold current is twice the rheobase (Lapicque 1907). The average chronaxie of 34 cells such as those shown in FIG. 6 was 407±45 μs for 1/x fits, 338±81 μs for power fits, and 212±28 μs for exponential fits. The average rheobase was 0.51±0.12 μA, 0.60±0.11 μA, and 0.76±0.16 μA, respectively. The fit quality was generally highest for power fits. Seven cells were from monkey, 7 from guinea pig, and 20 from rat and all responses were long-latency spikes. When the group of 20 rat cells was divided into those stimulated with the recording electrode and those stimulated at a neighboring site, no difference in chronaxie was found (p>0.5).

Figure 7:
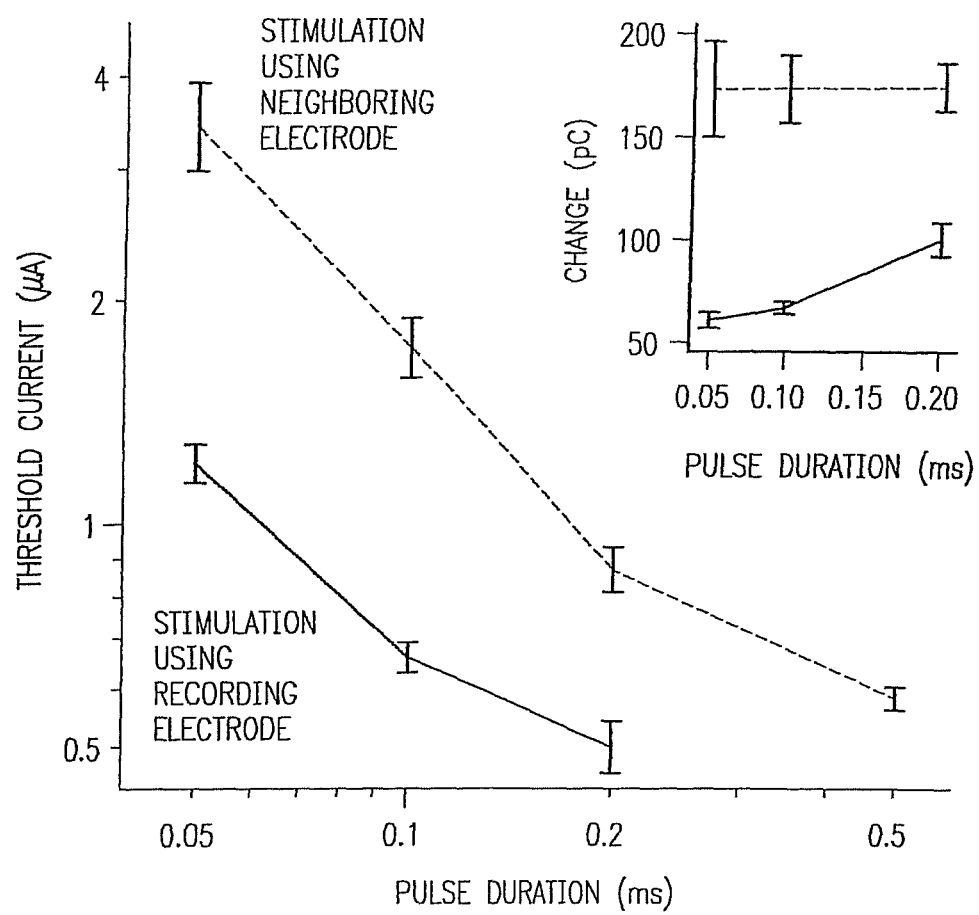
FIG. 7 is a graph of threshold current and charge.

To facilitate comparison of thresholds in a single species and to illustrate the influence of stimulation electrode position, FIG. 7 shows averaged data from 25 ganglion cells in rat. The cells were stimulated under identical conditions using electrodes with similar diameters (average 10.4±0.5 μm) and only long-latency responses were included. The solid line plots thresholds for stimulation at the recording electrode (13 cells), while the dashed line shows results from stimulation at a neighboring electrode (12 cells). As in FIG. 5A, eliciting a spike required several-fold higher currents when the site of stimulation was at an adjacent electrode. Since the charge delivered during the cathodic phase of the pulse is often used as a measure for stimulation strength, the inset plots charge thresholds for pulse durations up to 0.2 ms: charges were consistently below 200 pC, corresponding to charge densities below 0.25 mC/cm2.

To further corroborate the above notion that short- and long-latency spikes constitute doublet responses, we measured strength-duration curves of responses with latencies <2 ms. The average strength-duration relationship in 14 cells with short-latency spikes (latency 0.69±0.08 ms) was similar to that of long-latency responses: chronaxies determined from fit curves (as above) were 571±149 μs, 299±52 μs, and 311±113 μs; none of these values was significantly different from long-latency chronaxies (p>0.1; n=45 cells). These results suggest that the same neuronal element was excited in both short- and long-latency responses.

Frequency Dependence

Figure 8A:
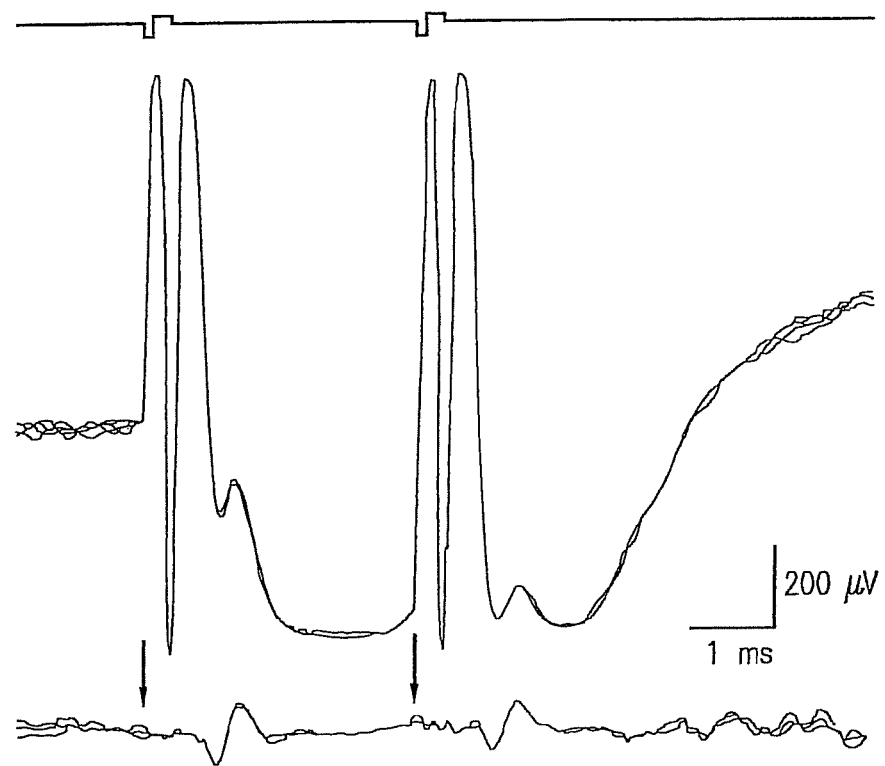
FIG. 8 A-C are waveforms showing frequency dependence of stimulation.

To mimic natural spike trains, a retinal implant must be capable of delivering pulses and evoke spikes at a wide range of stimulation frequencies. Furthermore, continual stimulation at higher frequencies may be a requirement for generating sustained percepts of light. We tested stimulation at pulse frequencies of up to several hundred Hz. To examine high-frequency responses, two closely spaced pulses were applied, with the inter-pulse interval corresponding to frequencies of up to 200-300 Hz. High-frequency stimulation was deemed successful when spikes were evoked following the second stimulus pulse. Pulse pairs were applied for 10-20 seconds at intervals of 0.5 seconds and at stimulus strengths of about twice threshold. In 9 cells tested, spikes were evoked on the second pulse on 99±1% of trials at 100 Hz, and 94±4% at 200 Hz. Three cells were stimulated with 300 Hz pulse pairs and all responded at >90% of trials. All responses were short-latency spikes (latency 0.8±0.2 ms). Data from such an experiment is shown in FIG. 8A: a super-threshold 300 Hz pulse pair reliably produced two short-latency spikes, more clearly seen in the artifact-subtracted traces shown below. A superposition of several stimulus trials is shown to demonstrate repeatability. In 4 cells, TTX was added to the bath solution to facilitate artifact subtraction and spike detection (not shown).

Figure 8B:
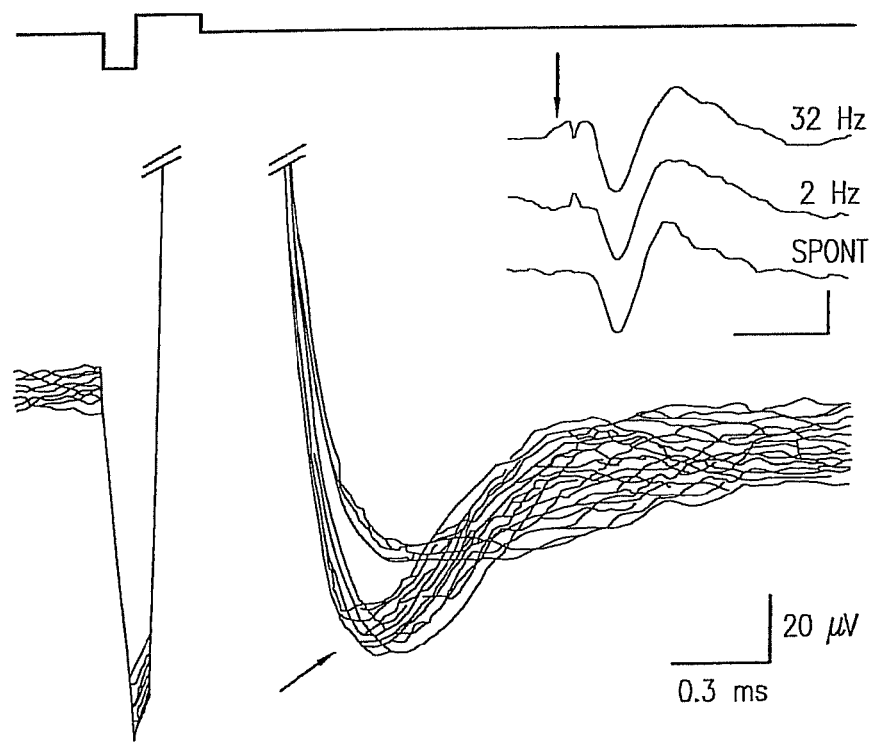

To test responses to brief periods of sustained high-frequency stimulation, 9 cells were continuously stimulated for 5-20 seconds at frequencies of up to 100 Hz. FIG. 8B shows an example of responses to over 70 stimulus pulses near spike threshold, delivered at 32 Hz. Short-latency spikes were evoked on roughly half of the trials (arrow) and were used to subtract the artifact (inset). 32 Hz stimulation evoked spikes indistinguishable from those produced by 2 Hz stimulation or spontaneous activity.

Figure 8C:
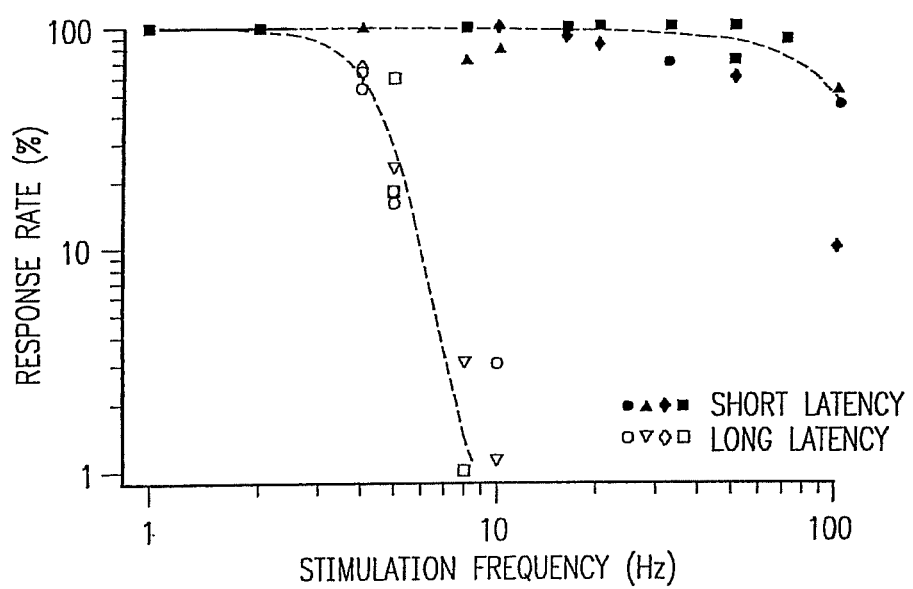

Response rates, defined as the number of evoked spikes in a stimulation period, were measured at sustained pulse frequencies of up to 100 Hz at stimulus strengths of about twice threshold (FIG. 8C). Short-latency spikes (closed symbols) showed a slight reduction of the response rate at 50 Hz (<20%) and a significant drop at 100 Hz. We also observed a gradual reduction in spike amplitude throughout the stimulation period at frequencies above about 32 Hz (not shown). Strikingly, long-latency responses (open symbols) were robust only up to 5 Hz and virtually no spikes were observed above 10 Hz. This observation was corroborated in one cell with a short-latency spike (0.7 ms) which was followed by a spike at latency 5 ms: stimulation at low frequencies consistently evoked both responses, while only the short-latency spike was observed at frequencies above 8 Hz.

We conclude that short-latency spikes can be reliably evoked in ganglion cells at pulse frequencies up to about 50 Hz and that late spikes are suppressed at moderate frequencies.

Sustained Stimulation

Chronic retinal implants must be capable of delivering effective stimulation pulses over a period of many hours each day. To determine whether sustained low-frequency stimulation could reliably evoke spikes, we extended our stimulation period to the longest duration that was experimentally feasible.

Figure 9:
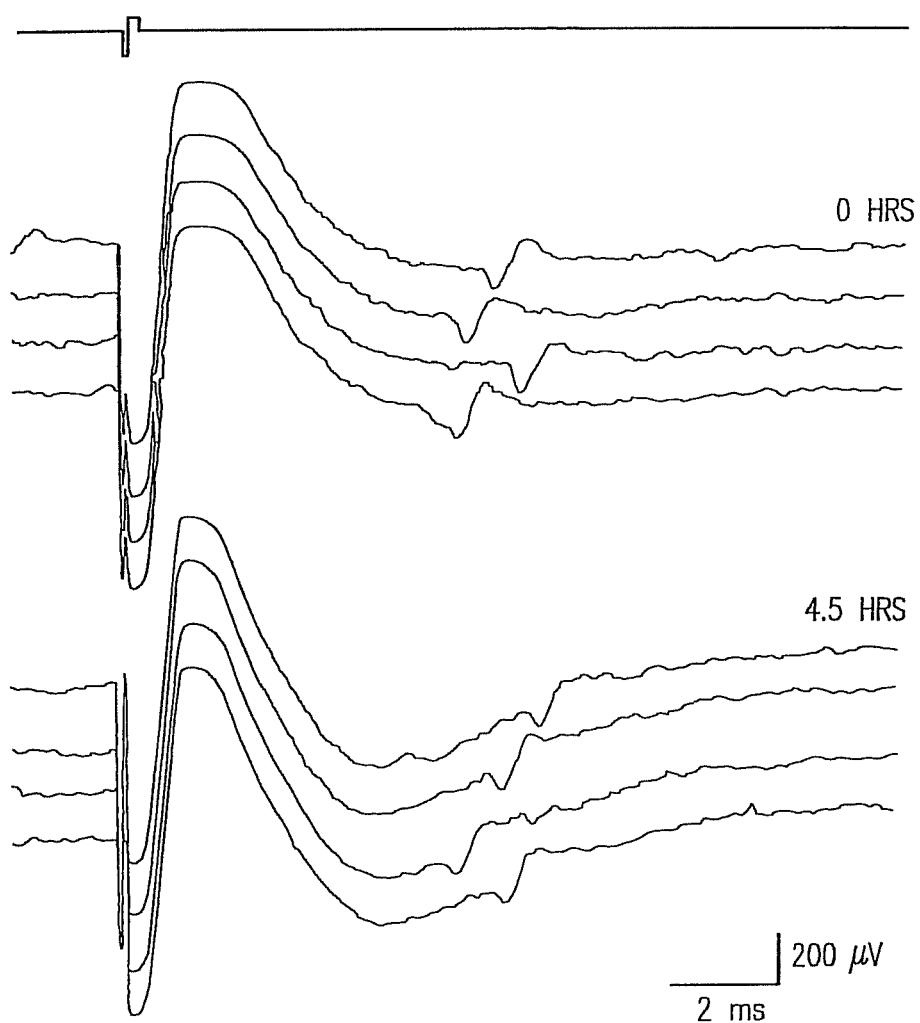
FIG. 9 is a waveform illustrating continuous low-frequency stimulation.

Two cells were continuously stimulated for 30 minutes, and two additional cells for 4.5 hours. The longest sustained stimulations were performed using 0.8 µA pulses with 0.1 ms duration, delivered at frequencies of 1-2 Hz, and corresponding to a charge density of about 0.04 mC/cm2 per pulse. FIG. 9 shows an example of spikes evoked before and after a 4.5 hours stimulation period: the cell showed robust responses after having been stimulated with over 16,000 pulses. A slight increase in threshold and spike latency (about 20%) was noted at the end of the stimulation period.

Multi-electrode Stimulation

To generate artificial vision, a functional retinal implant requires independent activation of many closely-spaced electrodes. To investigate responses to spatial stimulation patterns, the multi-electrode array was utilized to stimulate at several electrodes simultaneously. Our goal was to demonstrate that simultaneous activation of two or more nearby electrodes did not influence each other. If that were the case, spikes elicited during multi-electrode stimulation should not differ in threshold, shape, or number from individual stimulations.

Figure 10A:
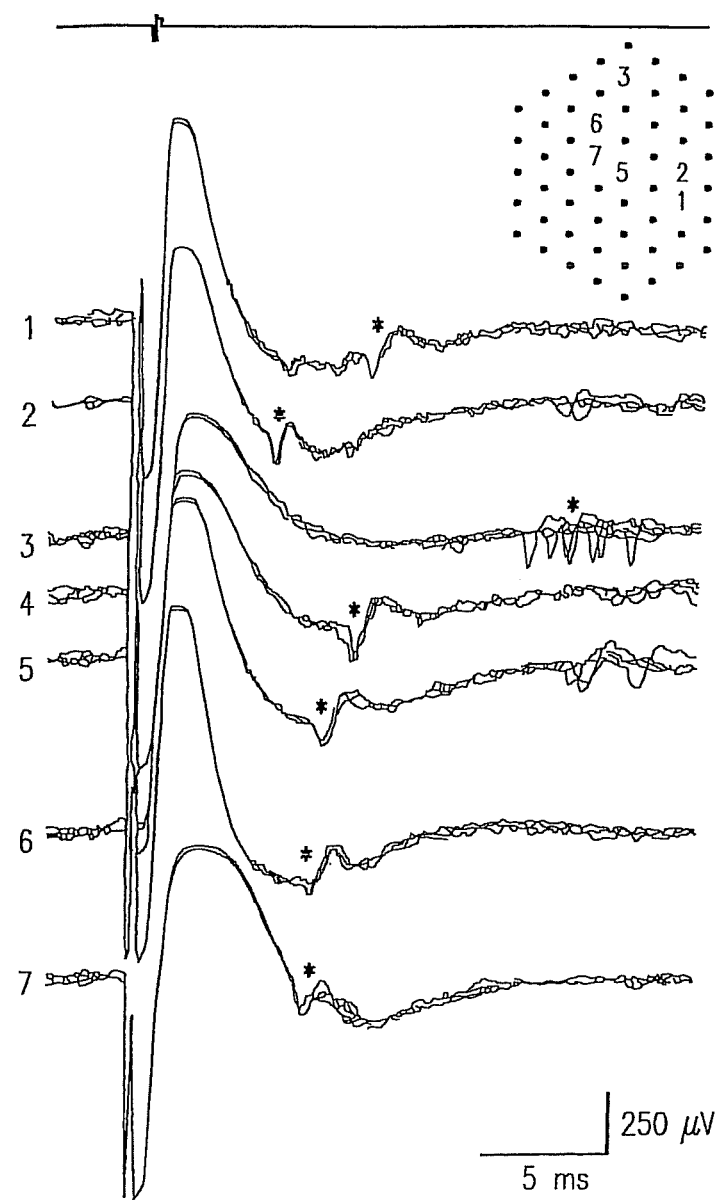
FIG. 10 A-B are waveforms illustrating multiple site stimulation.

We selected 7 sites which clearly showed evoked long-latency spikes when stimulated individually. These evoked spikes differed in spike shape and latency, but had similar thresholds. All 7 electrodes were subsequently activated simultaneously using 0.8 µA pulses (0.1 ms duration) and the responses recorded. FIG. 10A shows spikes evoked at these sites and their locations on the array. Simultaneous stimulation evoked seven distinct responses on seven spatially disparate electrodes.

Figure 10B:
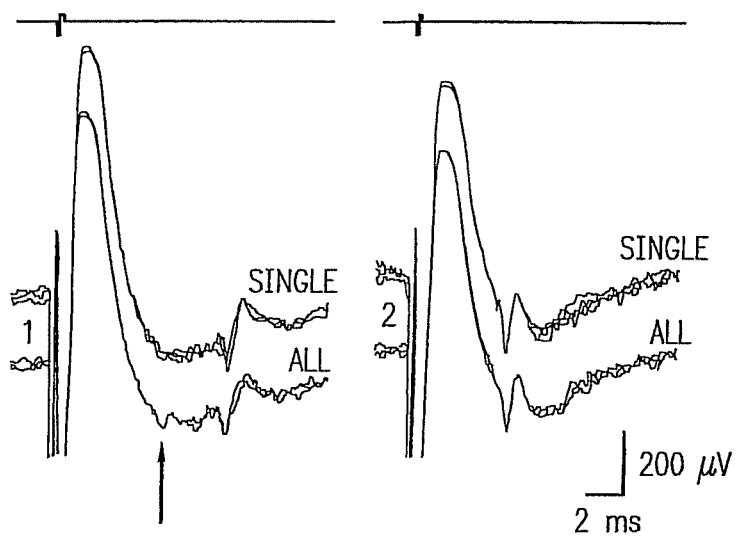

To establish that the spikes evoked by simultaneous stimulation did not differ from those evoked by individual stimulation, traces recorded at each electrode under both conditions were compared. Two examples are shown in FIG. 10B: individually evoked spikes (single) were identical to simultaneously evoked spikes (all) for both electrodes shown here. Furthermore, FIG. 10B demonstrates that stimulation at neighboring electrodes evoked independent responses. While this was expected given the low currents utilized here (see FIG. 5A), these data clearly establish that adjacent electrodes (1 and 2) did not influence each other during simultaneous stimulation. Only a small-amplitude deflection was recorded on electrode 1 at the latency of the spikes seen on electrode 2 (arrowhead), indicating that the cell stimulated by electrode 2 was probably located close enough to electrode 1 to be recorded as small spikes. To further ensure spatial precision, all 22 inactive electrodes surrounding the 7 active stimulating electrodes were inspected for spikes. While four adjacent electrodes showed small spikes that were recorded on one of the 7 stimulation electrodes, none recorded new spikes. Multi-electrode stimulation was performed 5 times using various electrode arrays and spatial patterns, with results very similar to the data presented above. We conclude that evoking independent spikes on multiple electrodes spaced 60 µm apart is feasible with minimal cross-electrode interaction.

Electrode Size

This study employed arrays with electrodes that varied in diameter between 6 and 25 µm. To determine the influence of electrode size on thresholds, stimulation results were compared in a set of 86 cells for which the exact platinum disk diameters of the stimulating electrode was measured. FIG. 11 shows thresholds as a function of electrode diameter, both for cells stimulated using pulse durations of 0.1 and 0.05 ms. Current, charge, current density, and charge density are plotted. All spikes were long latency spikes (average 7.6±0.3 ms).

Threshold current and charge (FIG. 11A, B) increased by a factor of 2-3 between the smallest and the largest diameters, indicating that with smaller electrodes, less current and charge injection was necessary to elicit spikes in ganglion cells. Conversely, current density and charge density (FIG. 11C, D) was drastically decreased for electrodes larger than 10-15 µm. Note that the lowest threshold values plotted here may have been overestimated since the minimal available current setting (0.6 µA) often evoked a super-threshold response.

Discussion

This study used dense arrays of small-diameter electrodes to electrically stimulate rat, guinea pig, and primate retina. We described the responses of individual ganglion cells to a wide range of pulse configurations and spatial stimulation patterns and showed that effective stimulation is feasible with high temporal and spatial precision. Our findings imply that the electrode size of future epiretinal prosthetics may safely approach the cellular dimensions of retinal ganglion cells.

Evoked Spikes

Long-latency spikes (>2 ms) were readily observable, while spikes with shorter latencies could only be observed with digital artifact subtraction. Note that this classification into "short" and "long" latencies differs somewhat from that of other researchers: Jensen et al. (2005) defines short as 3-5 ms and long as ≥9 ms; Stett et al. (2000) classifies spikes at latencies 1-10 ms as early and spikes at 10-20 ms as delayed. The definition of Crapper & Noel (1963) is more similar to the one used in this study: immediate spikes were defined as those around 0.5 ms latency and later responses as 5-15 ms. Early spikes. The earliest observed responses occurred within several hundred µs of stimulation onset and probably represent the immediate activation of the ganglion cell spike generator. Actual latencies are in effect shorter than the reported values by 50-100 µs due to a delay introduced by the amplifier circuitry. Further, if measured from the termination of the cathodic phase, true minimal latencies observed in this study amount to 50-150 µs. While these values are lower than the latencies in many studies, sub-millisecond spikes have been reported by a few authors (Crapper and Noell 1963; Grumet et al. 2000). Late spikes. We showed that evoked spikes at longer latencies are preceded by short-latency spikes.

Long-latency spikes can thus be used to infer short-latency spikes even when the magnitude of the pulse artifact confounds direct observations of early spikes. However, it is possible that thresholds for long-latency spikes are systematically overestimated, since short-latency responses typically occur at lower stimulation currents than doublet responses. Multi-spike responses are consistent with known intrinsic firing properties of ganglion cells, in which doublets or triplets in spike trains occur with interspike intervals of several ms (e.g. Devries and Baylor 1997). In our study, interspike intervals ranged from 4 to 16 ms, with the majority of long latency spikes occurring around 5-7 ms after the short-latency spikes. We favor the interpretation of long-latency spikes as part of a doublet response over other suggestions such as conduction delays (Jensen et al. 2005b) or intracellular charging mechanisms for the following reasons: the small electrodes and currents used here make activation several millimeters from the recording site exceedingly unlikely; in each case tested, every long-latency spike was preceded by a short-latency spike; and earlier studies have not employed artifact subtraction methods, thus seeing only later spikes.

Furthermore, long-latency spikes are only observed at stimulation frequencies below 10 Hz, suggesting that higher repetition rates suppress multi-spike bursts. Stimulation thresholds Safety of stimulation. An important prerequisite of implantable stimulators is their capability to deliver current that is safe, yet efficient. Unsafe stimulation can originate from two sources: electrochemical destruction of the stimulating electrode (such as corrosion), and neural tissue damage induced by toxic products near the electrode or by neuronal hyperactivity. Several electrochemical safety limits have been proposed, such as the often-stated non-gassing limit of 0.3-0.4 mC/cm2 for platinum electrodes (Brummer and Turner 1977). More recently, limits as low as 0.1 mC/cm2 for cathodic stimulation with platinum electrodes have been recommended (Rose and Robblee 1990).

Thresholds for tissue injury in cortex have been shown to arise from the synergistic interaction between charge and charge density: as the charge is increased, the charge density for safe stimulation decreases (McCreery et al. 1986; McCreery et al. 1990; Merrill et al. 2005). The McCreery data show that no histologically detectable damage is produced with low-charge stimulation (<50 nC) even when the charge density is >1 mC/cm2, while for pulses delivering a higher charge (1 μC), the damage threshold is <0.1 mC/cm2. In the absence of detailed threshold measurements, concerns have been raised regarding the feasibility of using small-diameter electrodes in human patients, since they have been suggested to require much higher charge densities for threshold stimulation than large electrodes (Brummer et al. 1983; Loeb et al. 1983; Greenberg 1998). However, we found in this study that threshold stimulus pulses are characterized by low currents (around 1 μA), low charge injection (around 100 pC) and low charge densities (around 0.1 mC/cm2) despite the small electrode size. Several cells had threshold charge densities of less than 0.03 mC/cm2, an order of magnitude lower than the platinum electrode safety limit. Furthermore, while we have used the geometric electrode area to calculate current and charge densities, the effective electrode area likely was significantly larger. Electroplated platinum tends to deposit in granular surface structures which greatly increase the area of metal in contact with the solution. It has been reported that the fractal-like platinum deposits can increase the surface area by up to 100 times (Kim and Oh 1996; Mathieson et al. 2004). Thus, all density values reported here should be considered upper limits, further reducing the likelihood of electrochemical electrode damage.

Our results complement data recently reported for small-diameter needle electrodes, which have described threshold charge densities between 0.15 and 0.3 mC/cm2 (Wyatt et al. 1994; Rizzo et al. 1997; Jensen et al. 2003; Wilms et al. 2003). Distance between electrode and cells. One factor contributing to the low thresholds in this study is the tight contact between electrodes and tissue. This was a requirement in our experiments since extracellular spikes cannot be recorded without close juxtaposition of the retina to the array. Novel techniques to minimize the gap between retina and epiretinal implant are being developed (Schanze et al. 2002; Johnson et al. 2004) and may ensure close contact in future prosthetic devices. Optimal electrode size. We observed lower threshold current and charge for the smaller electrodes in this study than for the larger ones (see FIG. 11). However, the resulting charge density is increased for smaller electrodes. As electrode diameter drops below about 10 μm, the decrease in surface area outweighs the current decrease. It has been suggested that for electrodes smaller than the cellular size (about 10 μm) the electric field is concentrated in too small an area for effective stimulation (Palanker et al. 2004). Thus, electrode diameters around 10-15 μm may be the optimal size for selective single cell stimulation and might be an ideal compromise between excellent spatial resolution and high charge density. This size range would also have less stringent requirements on the distance between electrode and cells, since stimulation with <10 μm electrodes is disproportionately more sensitive to this distance (Palanker et al. 2004). Clearly, this issue will need to be re-addressed once technical advances in retinal prosthetics call for even smaller electrodes as the ratio of electrodes to ganglion cells approaches 1. Spatial resolution. One consequence of the low required stimulation strengths was the exceedingly localized nature of stimulation: excited cells were limited to a narrow radius around the stimulating electrode and pharmacology experiments further confirmed that ganglion cells were directly activated: spikes were not suppressed in the presence of CNQX, APV, and kynurenate, which block excitatory transmission in the retina (Fujimoto and Toyoda 1991; Stett et al. 2000). This is a much more local effect than can be achieved with larger electrodes: indirect spikes sensitive to synaptic blockers have been reported for 125 μm electrodes (Jensen et al. 2002; Ziv et al. 2002) and larger electrodes (Greenberg 1998; Shimazu et al. 1999). Our results from simultaneous stimulation using multiple electrodes further confirm that the current spread in the plane of the electrode array is small enough to allow for independent activation of cells using neighboring stimulation electrodes.

Thresholds increase with the distance between stimulating and recording electrode on the array (see FIG. 5A). The observed increases are similar to those of the cathodal stimulation map reported by Jensen et al. (2003): stimulating about 60 μm away from the center of the receptive field required 2-8 times more current to elicit a spike. We conclude from these observations that retinal implants with small electrodes can achieve a high spatial resolution, since the low applied currents activate single (or at most a few) ganglion cells.

Chronaxies and Site of Activation.

The use of pulses significantly longer than chronaxie contributes little to the evoked response, stipulating pulse durations smaller than chronaxie to insure that most of the applied charge contributes to evoking a response (Tehovnik 1996). Thus, from the chronaxies measured in this study (around 100-400 μs) we conclude that optimal pulse durations should not exceed this range. The measured values are similar to those reported in other studies (Crapper and Noell 1963; Greenberg 1998; Grumet et al. 2000; Jensen et al. 2005b) and can further be used to identify the neuronal element most likely excited by electrical stimulation. Our chronaxies match those reported for activation of axons (Nowak and Bullier 1998; Grumet et al. 2000; Holsheimer et al. 2000), since cell bodies and dendrites have chronaxies of 1-10 ms (Ranck 1975; Holsheimer et al. 2000). Because the initial axon segment near somas is more excitable than cell bodies (Porter 1963; Nowak and Bullier 1998; Greenberg et al. 1999; Schiefer and Grill 2002), the juxtasomal electrode used here likely activates this initial region on the axon and action potentials subsequently back propagate a short distance to elicit the recorded somatic spike. Computational models suggest that excitation occurs near the junction of ganglion cell soma and axon or slightly more distal on the axon (Fohlmeister and Miller 1997; McIntyre and Grill 1999; Schiefer and Grill 2002).

It is difficult to experimentally rule out the activation of passing axons, in particular since tests designed to identify antidromic responses (Fuller and Schlag 1976) would more distinguish between initial axon segment excitation and more distant axon activation. Nevertheless, activation of passing axons is deemed less likely by the fact that ganglion cell axons have high thresholds away from their initial segment (Loeb et al. 1983). Since in retinal ganglion cells of most mammals (including human and rat) the axon remains unmyelinated within the retina, sodium channels are found uniformly throughout the distant unmyelinated region (Boiko et al. 2003). At the initial axon segment, however, the density of sodium channels is exceptionally high (Wollner and Catterall 1986), with clustering of the Nav1.6 subunit in particular (Boiko et al. 2003). This difference in channel density between the initial and distant region can amount to an order of magnitude or more (Ritchie et al. 1976; S. R. Levinson, personal communication). Like the nodes of Ranvier in myelinated fibers (McIntyre and Grill 2000), the initial portion of unmyelinated axons constitutes the most likely site of electrical excitation, perhaps at the "thin segment" 10-40 μm from the cell body (Fohlmeister and Miller 1997; Boiko et al. 2003).

Comparative Literature Analysis

To discuss data from this study in the context of previous work, a comprehensive review of the published literature was composed. Table 1 summarizes 32 studies that have reported epiretinal stimulation thresholds. These studies span several orders of magnitude in electrode size and can thus be used to elucidate threshold trends. Several key parameters have been graphed in FIG. 12, along with best fit lines and correlation coefficients. To facilitate comparison of different electrode geometries across studies, threshold parameters were plotted against the geometric electrode surface area (see Methods).

Variability.

Several factors contribute to the relatively wide scatter of points in FIG. 12. Threshold was defined inconsistently from study to study, spanning the range of 50 to 90% probability of eliciting a spike, cortical recordings, and human percept reports. Furthermore, while the majority of studies utilized charge-balanced biphasic pulses, several reported monophasic stimulation (typically cathodal), leading to lower thresholds in some cases. Moreover, human studies (open symbols) usually involved degenerated retinas, while animal studies were typically performed on normal tissue. Finally, studies which measured retinal responses by monitoring cortical activity (triangles) may have overestimated spike thresholds in ganglion cells, since the concerted activity of many cells is typically required for a cortical response.

Parameter Trends.

Figure 11A:
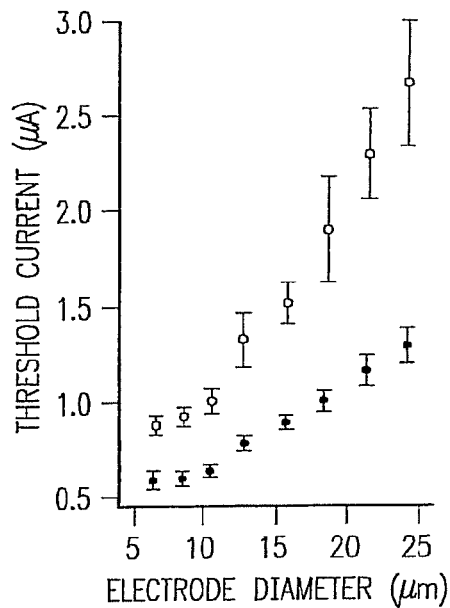
FIG. 11 A-D are graphs showing dependence of threshold on electrode size.
Figure 11B:
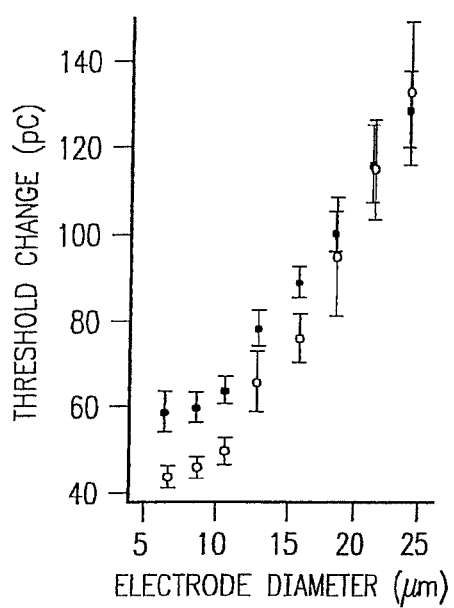
Figure 11C:
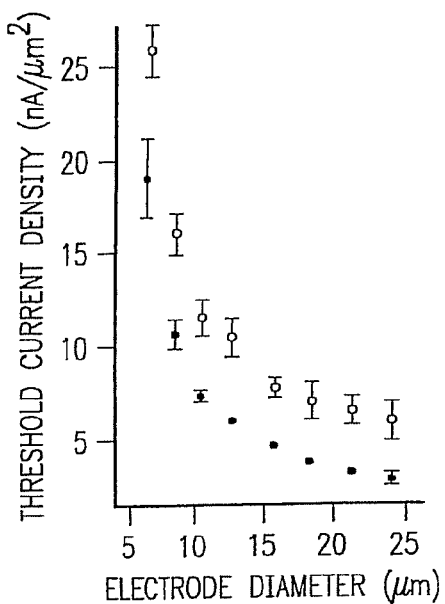
Figure 11D:
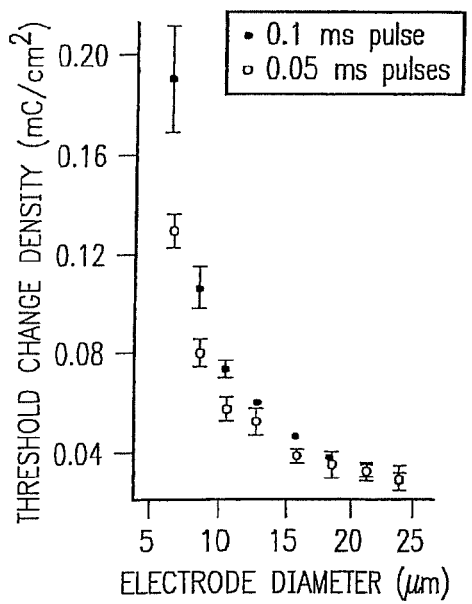
Figure 12A:
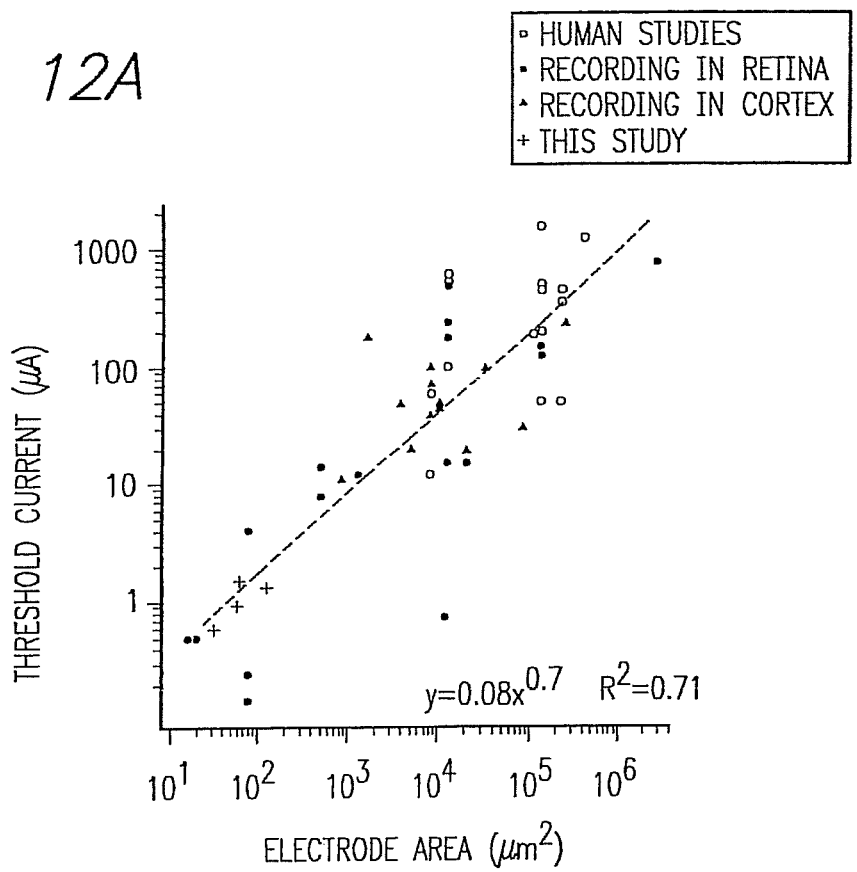
FIG. 12 A-D are graphs showing a summary of threshold information from literature analysis.
Figure 12B:
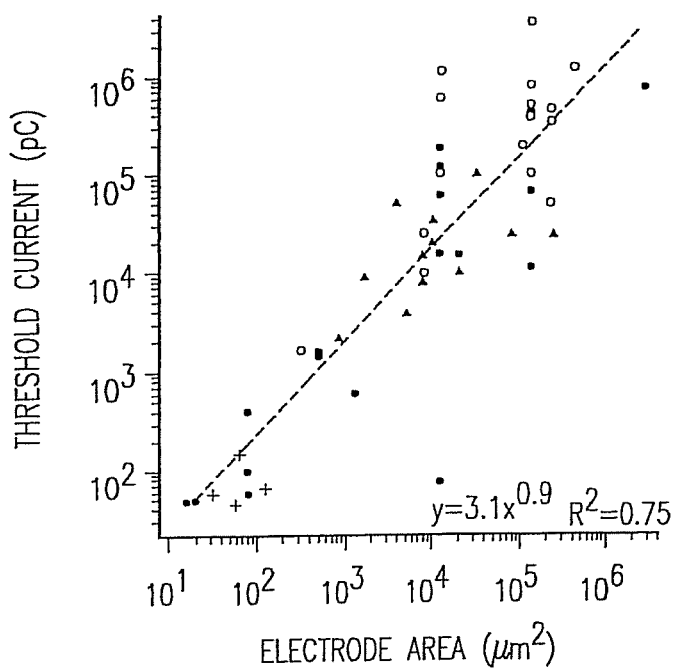
Figure 12C:
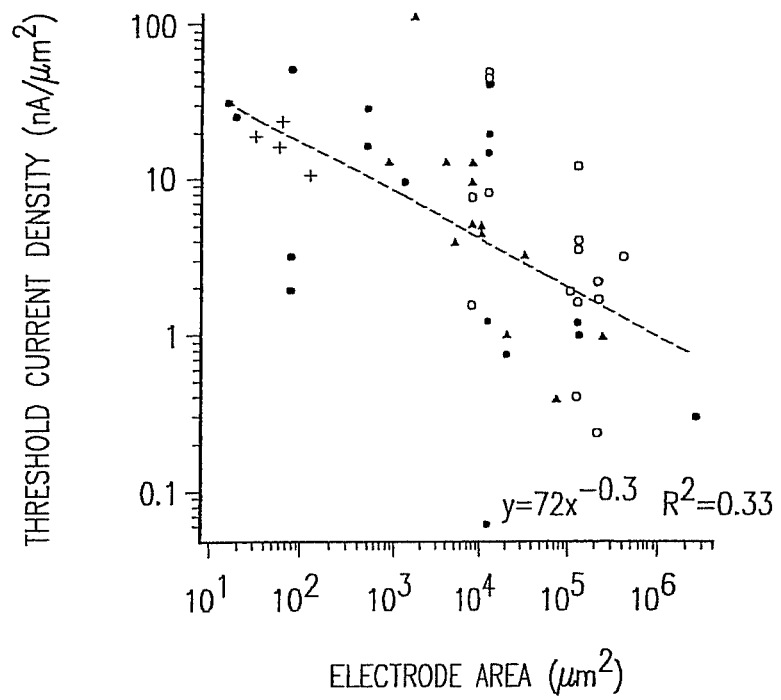
Figure 12D:
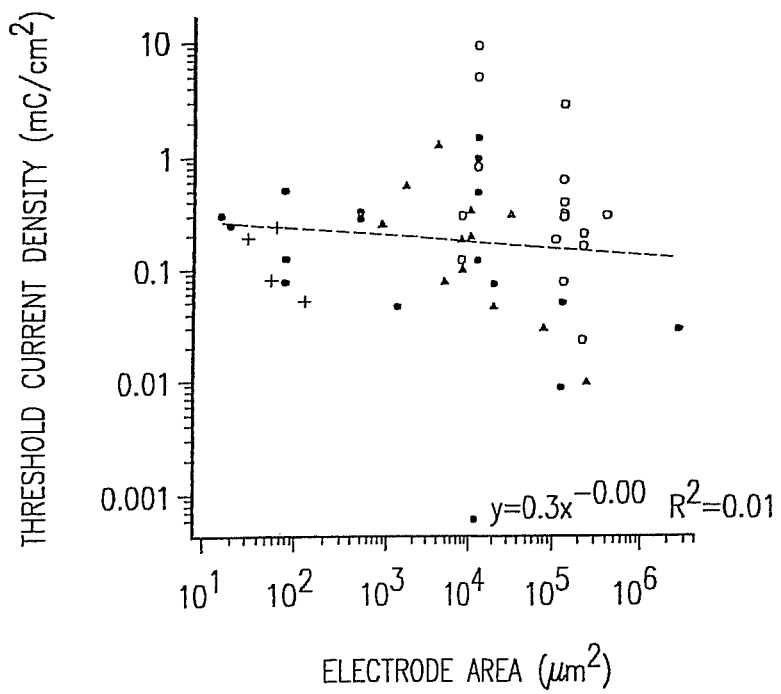

Both threshold current and charge (FIG. 12A, B) decrease dramatically as electrode size is reduced. Correlation was highest for threshold charge, since it takes into account both current and pulse duration, which varied across studies. These trends confirm that smaller electrodes require several orders of magnitude lower currents to elicit responses. They also mirror the results found within this study over a much more narrow range of electrode sizes: current and charge thresholds were small for small stimulating electrodes and large for large electrodes (FIG. 11A, B). Current density also increases somewhat when electrode size is reduced (FIG. 12C), but such a trend is not seen in the plot of charge density thresholds (FIG. 12D). While the large variability does not permit an accurate fit to the data, there is no definitive change of charge density with electrode size, such as is seen for threshold charge over 4-5 orders of magnitude. In fact, charge density is virtually independent of electrode size for electrodes smaller than 104 μm2 (disk diameter about <100 μm). This trend is in contrast to the increased charge densities observed for the smallest electrodes used in this study (see FIG. 11D), which is probably due to an effect restricted to electrodes smaller than ~10 μm diameter (see above).

Representative data from this study (monkey and rat) have been included in FIG. 12 and fit well with the trends established by the published literature. Our data substantiate the main conclusion from this analysis: small electrodes require much less charge injection for threshold stimulation than larger electrodes, but the accompanying increase in charge density is almost negligible.

Stimulation Safety.

Since both charge and charge density must be considered when discussing stimulation safety (Merrill et al. 2005), FIG. 13 shows a plot of both parameters for the same set of studies. Two types of safety limits were included (dotted lines): the often used electrochemical limits for platinum electrodes (0.35 and 0.1 mC/cm2) and the limits for neural injury from cortical stimulation data (k=1.7 and 2.0; see Methods). To show the spread of thresholds measured in this study, FIG. 13 includes data points for all cells stimulated using 0.05 ms pulses and electrodes with diameters between 6 and 25 μm (crosses). Most human studies (and several animal studies) fall near or outside of the safe region formed by the limit curves, possibly because degenerated retina requires higher currents to produce phosphenes in humans. This plot further validates our claim that the small electrodes used in this study can safely stimulate mammalian retina: except for the data collected using the smallest electrodes, most thresholds are well within all safety limits.

Outlook

The purpose of this study was to elucidate basic stimulation parameters to test whether a future generation of implants could incorporate a design using significantly smaller electrodes than are presently available. We used planar microelectrode arrays that closely resemble those currently in use for chronic human testing (Humayun et al. 2003), but contain much smaller electrodes at a much smaller electrode spacing. We suggest that future implants could directly activate ganglion cells instead of affecting large areas of retina by indirect stimulation, making possible a reasonable spatial resolution of artificial sight. One can envision high-resolution arrays containing thousands of stimulation sites with diameters around 10-20 μm and separation between electrodes of 20-60 μm. While years away, results from this study suggest that there is no fundamental hindrance to the feasibility of such a device. Once implanted, the stimulus parameters can be adjusted to stimulate individual or small overlapping groups of ganglion cells, depending on the desired phosphene size. By utilizing low currents, activation of axon bundles can be avoided. As a next step toward the development of such implants, further experiments using small electrodes with degenerated retina are warranted.

Figure 14:
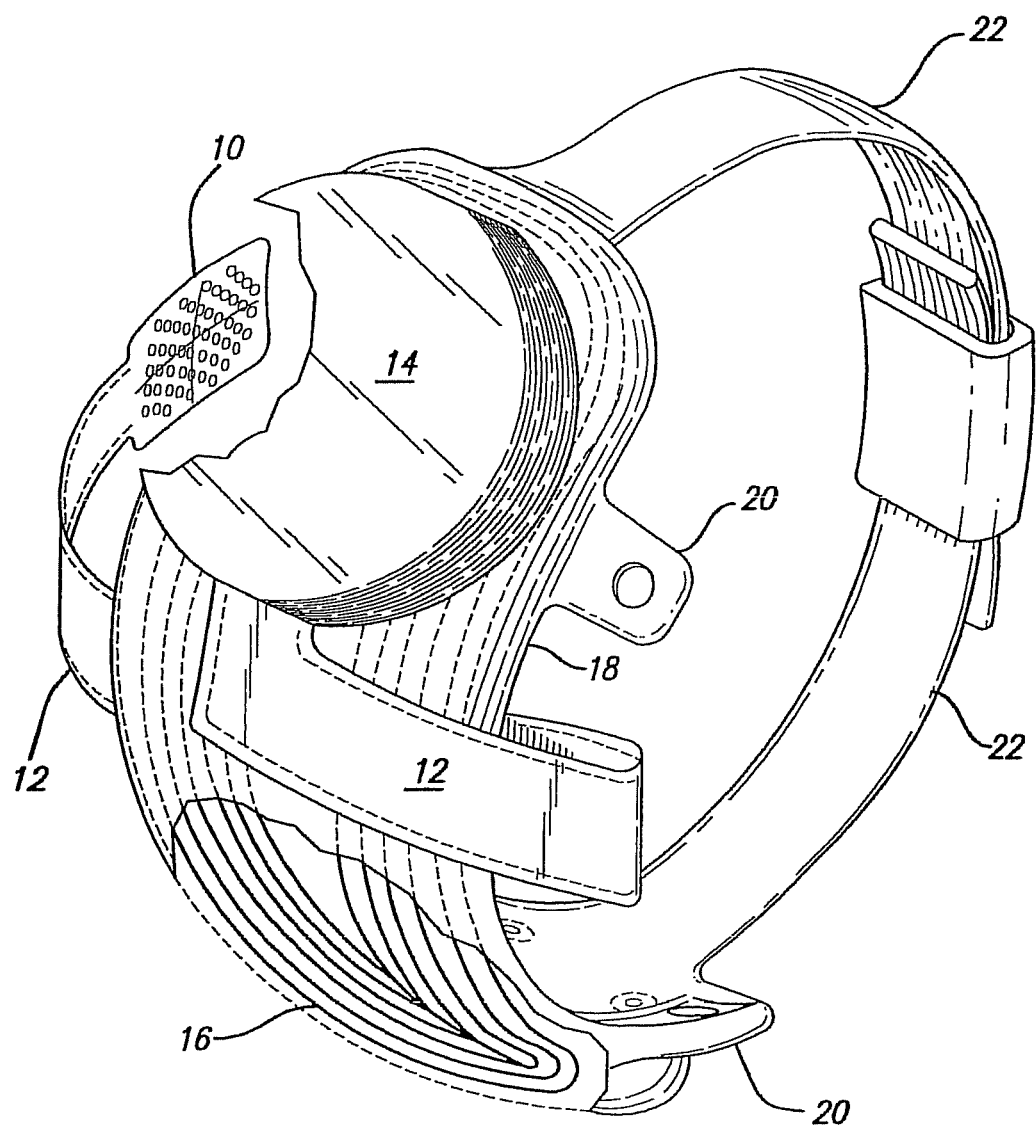
FIG. 14 is a perspective view of the implanted portion of the preferred retinal prosthesis.

FIG. 14 shows a perspective view of the implanted portion of the preferred retinal prosthesis. While the invention has broad applicability to neural stimulation, the preferred embodiment is a retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, the secondary inductive coil 16, and the electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

Since the retina is spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

The preferred prosthesis includes an external portion (not shown) which includes a camera, video processing circuitry and an external coil for sending power and stimulation data to the implanted portion.

Figure 15:
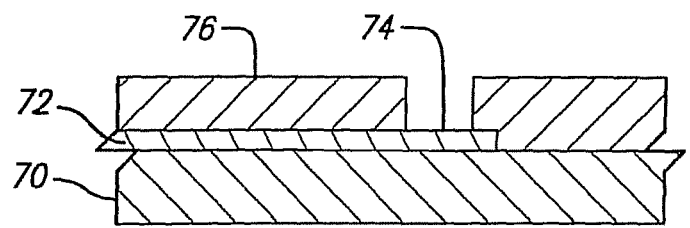
FIG. 15 is an enlarged view of a single electrode within the flexible circuit electrode array.

Referring to FIG. 15, the flexible circuit electrode array (10 in FIG. 14) is manufactured in layers. A base layer of polymer 70 is laid down, commonly by some form of chemical vapor deposition, spinning, meniscus coating or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIG. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 16:
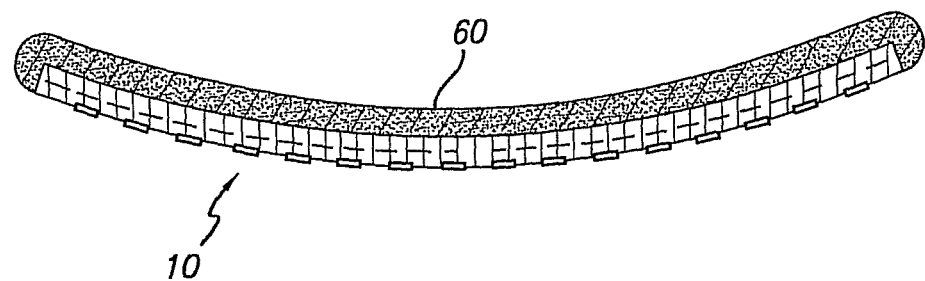
FIG. 16 depicts a flexible circuit array with a protective skirt or bumper bonded to the back side of the flexible circuit array and molded around the edges of the flexible circuit array and flush with the front side of the array.

FIG. 16 shows a flexible circuit electrode array 10, with the skirt or bumper 60, flush with the front side of the flexible circuit electrode array 10 rather than extending beyond the front side. If there is sufficient bond with the flexible circuit electrode array 10, it may advantageous to thin or remove portions of the skirt 60 material for weight reduction.

A first aspect of the invention is an electrode array for stimulating visual neurons comprising: a non-conductive body; a plurality of conductive electrodes wherein the electrode are less than 20 µm in size and less than 60 µm apart; and means for supporting the body in close proximity to visual neurons.

A second aspect of the invention is the electrode array according to the first aspect, wherein the electrodes are arranged hexagonally.

A third aspect of the invention is the electrode array according to the first aspect, wherein the non-conductive body is a fluoro-polymer.

A fourth aspect of the invention is the electrode array according to the first aspect, wherein the electrodes are arranged in a pattern longer in one dimension than the other dimension; and wherein the one dimension corresponds to horizontal in a visual scene.

A fifth aspect of the invention is a flexible circuit electrode array adapted for neural stimulation comprising: A polymer base layer; Metal traces deposited on the polymer base layer, including electrodes suitable to stimulate neural tissue; and A polymer top layer deposited on the polymer base layer and the metal traces;

Wherein the polymer top layer defines openings smaller than the electrodes to overlap the electrodes.

A sixth aspect of the invention is a flexible circuit electrode array adapted for neural stimulation comprising: a polymer base layer; metal traces deposited on the polymer base layer, including electrodes suitable to stimulate neural tissue; and a polymer top layer deposited on the polymer base layer and the metal traces; wherein the electrodes are less than 20 µm in size and less than 60 µm apart.

A seventh aspect of the invention is the flexible circuit electrode array according to the sixth aspect, wherein the polymer base layer, the metal traces and the polymer top layer are curved to approximately the curvature of an eye.

An eighth aspect of the invention is the flexible circuit electrode array according to the sixth aspect, further comprising at least one bumper bonded to a peripheral edge of the flexible circuit electrode array.

A ninth aspect of the invention is the flexible circuit electrode array according to the sixth aspect, further comprising a narrowed portion in a flexible circuit cable portion of the flexible circuit electrode array.

A tenth aspect of the invention is the flexible circuit electrode array according to the sixth aspect, further comprising a stress relief membrane suitable for attachment of the flexible circuit electrode array, wherein the stress relief membrane is a more compliant material than the polymer base layer.

An eleventh aspect of the invention is the flexible circuit electrode array according to ninth aspect, wherein the narrowed portion is suitable to pierce a sclera.

A twelfth aspect of the invention is the flexible circuit electrode array according to the eleventh aspect, wherein the narrowed portion is a diagonal fold in a flexible circuit cable portion of the flexible circuit electrode array.

A thirteenth aspect of the invention is the flexible circuit electrode array according to the twelfth aspect, where the diagonal fold is across a dogleg in the flexible circuit electrode array.

A fourteenth aspect of the invention is the flexible circuit electrode array according to the thirteenth aspect, further comprising bond pads coupled to the metal traces on an end of the flexible circuit electrode array opposite to the electrodes and openings in the polymer top layer for the electrodes and the bond pads.

A fifteenth aspect of the invention is the flexible circuit electrode array according to the eighth aspect, where the bumper is a continuous skirt covering at least of portion of the flexible circuit electrode array.

A sixteenth aspect of the invention is the flexible circuit electrode array according to the eighth aspect, where the bumper is a continuous skirt covering at least of portion of a cable portion of the flexible circuit electrode array.

A seventeenth aspect of the invention is the flexible circuit electrode array according to the sixteenth aspect, further comprising a sleeve at least partially covering a flexible circuit cable portion of the flexible circuit electrode array.

An eighteenth aspect of the invention is the flexible circuit electrode array according to the seventeenth aspect, wherein the sleeve and the bumper are a continuous body.

A nineteenth aspect of the invention is the flexible circuit electrode array according to the sixth aspect, wherein the polymer base layer, the metal traces and the polymer top layer for a continuous electrode array and flexible circuit cable where the flexible circuit cable forms a partial loop to resist transmission of forces through the flexible circuit cable.

A twentieth aspect of the invention is the flexible circuit electrode array according to the sixth asepct, wherein the electrodes are arranged in a hexagonal pattern.

Accordingly, what has been shown is an improved method of stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of making a flexible electrode array for retinal stimulation comprising:
    depositing a polymer base layer on a flat substrate forming bond pad portion, a cable portion, and an array portion;
    depositing metal on the polymer base layer;
    patterning the metal to form metal bond pads in the bond pad portion at an end, metal electrodes in the array portion at an opposite end and metal traces in the cable portion between the metal bond pads and metal electrode connecting the metal bond pads to the metal electrodes, the electrodes being less than 20 μm in diameter and less than 60 μm apart and wherein adjacent electrodes are arranged in a hexagon around a single adjacent central electrode;
    depositing a polymer top layer on the polymer base layer, the metal electrodes and the metal traces forming the flexible circuit electrode array;
    forming microwells in the polymer top layer and plating platinum in the microwells;
    removing the flexible circuit electrode array from the flat substrate;
    molding the flexible circuit electrode array portion in an approximately concave spherical mold to form the array portion in an approximately convex spherical shape to approximate the curvature of target retinal tissue and make the curved surface suitable to contact the retinal tissue; and
    forming a second polymer, softer than said polymer top layer, over said polymer top layer; and
    wherein the cable portion is suitable to pass through a sclera and the bond pad portion connect to an electronics package and receiver coil outside the eye and mounted to a lateral side of the eye.

2. The method according to claim 1, wherein the step of depositing the polymer base layer and the polymer top layer is depositing polyimide.

3. The method according to claim 1, wherein the step of depositing the polymer base layer and the polymer top layer is depositing silicone.

4. The method according to claim 1, wherein the step of depositing the polymer base layer and the polymer top layer is depositing fluoropolymer.

5. The method according to claim 1, further comprising bonding at least one bumper to a peripheral edge of the flexible circuit electrode array.

6. The flexible circuit electrode array according to claim 5, where the bumper is a continuous skirt covering at least of portion of the flexible circuit electrode array.

7. The method according to claim 1, further comprising bonding a stress relief membrane, suitable for attachment to neural tissue, to the flexible circuit electrode array, wherein the stress relief membrane is a more compliant material than the polymer base layer.

8. The method according to claim 1, wherein the step of patterning is patterning the electrodes in a hexagonal pattern.

9. The flexible circuit electrode array according to claim 1, wherein the adjacent electrodes arranged in a hexagon around a single adjacent central electrode are equally spaced.

* * * * *